US007727712B2

(12) United States Patent
Van Nest et al.

(10) Patent No.: US 7,727,712 B2
(45) Date of Patent: Jun. 1, 2010

(54) METHODS OF SUPPRESSING HEPATITIS VIRUS INFECTION USING IMMUNOMODULATORY POLYNUCLEOTIDE SEQUENCES

(75) Inventors: Gary Van Nest, Martinez, CA (US); Joseph J. Eden, Jr., Danville, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 741 days.

(21) Appl. No.: 10/357,760

(22) Filed: Feb. 3, 2003

(65) Prior Publication Data

US 2003/0216340 A1 Nov. 20, 2003

Related U.S. Application Data

(63) Continuation of application No. 09/802,370, filed on Mar. 9, 2001, now abandoned.

(60) Provisional application No. 60/188,301, filed on Mar. 10, 2000.

(51) Int. Cl.
*C12Q 1/70* (2006.01)
(52) U.S. Cl. .............. 435/5; 424/278.1; 424/184.1
(58) Field of Classification Search ................ 514/44; 424/1.11, 85.1, 85.2, 85.4, 278.1; 435/5
See application file for complete search history.

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,453,496 A | 9/1995 | Caruthers et al. | |
| 5,616,461 A | 4/1997 | Schaffer et al. | |
| 5,663,153 A | 9/1997 | Hutcherson et al. | |
| 5,723,335 A | 3/1998 | Hutcherson et al. | |
| 5,849,719 A | 12/1998 | Carson et al. | |
| 5,874,089 A | 2/1999 | Schlegel et al. | |
| 6,174,872 B1 | 1/2001 | Carson et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,498,148 B1 | 12/2002 | Raz | |
| 6,514,948 B1 | 2/2003 | Raz et al. | |
| 6,534,062 B2 | 3/2003 | Raz et al. | |
| 6,552,006 B2 | 4/2003 | Raz et al. | |
| 6,613,751 B2 | 9/2003 | Raz et al. | |
| 7,157,437 B2 | 1/2007 | Van Nest | |
| 2001/0046967 A1 | 11/2001 | Van Nest | |
| 2002/0028784 A1 | 3/2002 | Nest | |
| 2002/0098199 A1 | 7/2002 | Van Nest et al. | |
| 2002/0107212 A1 | 8/2002 | Nest et al. | |
| 2003/0050263 A1 | 3/2003 | Krieg et al. | |
| 2003/0092663 A1 | 5/2003 | Raz | |
| 2004/0009942 A1 | 1/2004 | Van Nest | |
| 2004/0030118 A1 | 2/2004 | Wagner et al. | |
| 2005/0059626 A1 | 3/2005 | Van Nest et al. | |
| 2005/0101554 A1 | 5/2005 | Krieg et al. | |
| 2007/0060540 A1 | 3/2007 | Van Nest | |

FOREIGN PATENT DOCUMENTS

| | | |
|---|---|---|
| EP | 468520 A2 | 1/1992 |
| WO | WO 96/02555 A1 | 2/1996 |
| WO | WO 97/28259 A1 | 8/1997 |
| WO | WO 98/16247 A1 | 4/1998 |
| WO | WO 98/18810 A1 | 5/1998 |
| WO | WO 98/37919 A1 | 9/1998 |
| WO | WO 98/40100 A1 | 9/1998 |
| WO | WO 98/52581 A1 | 11/1998 |
| WO | WO 98/52962 A1 | 11/1998 |
| WO | WO 98/55495 A2 | 12/1998 |
| WO | WO 98/55495 A3 | 12/1998 |
| WO | WO 98/55609 A1 | 12/1998 |
| WO | WO 99/11275 A2 | 3/1999 |
| WO | WO 99/11275 A3 | 3/1999 |
| WO | WO 99/33488 A2 | 7/1999 |
| WO | WO 99/33488 A3 | 7/1999 |

(Continued)

OTHER PUBLICATIONS

De Francesco et al. Challenges and successes in developing new therapies of hepatitis C. Nature, 2005, vol. 436, 953-960.*
Hahn. Subversion of immune responses by hepatitis C virus: immunomodulatory strategies beyond evasion? Current opinion in Immunology, 2003, vol. 15, 443-449.*
Knipe DM, Howley PM, eds. Fields virology. 4th ed. vol. 1. Philadelphia: Lippincott Williams & Wilkins, 2001, 1004-1016 and 1127-1161.*
Mutwiri et al. Biological activity of immunostimulatory CpG DNA motifs in domestic animals. Veterinary Immunology and Immunopathology, 2003, vol. 91, 89-103.*
Krieg et al. CpG motif in bacterial DNA and their immune effects. Annu. Rev. Immunol., 2002, vol. 20, 709-760.*

(Continued)

*Primary Examiner*—Emily M. Le
(74) *Attorney, Agent, or Firm*—Morrison & Foerster LLP

(57) ABSTRACT

Methods are provided for the treatment of hepatitis B virus (HBV) and hepatitis C virus (HCV) infections. A polynucleotide comprising an immunostimulatory sequence is administered to a individual who has been exposed to or infected by HBV and/or HCV. The polynucleotide is not administered with a HCV or HBV antigen. Administration of the polynucleotide results in amelioration of symptoms of HBV and/or HCV infection.

5 Claims, 2 Drawing Sheets

FOREIGN PATENT DOCUMENTS

| | | |
|---|---|---|
| WO | WO 99/33868 A2 | 7/1999 |
| WO | WO 99/33868 A3 | 7/1999 |
| WO | WO 99/51259 A2 | 10/1999 |
| WO | WO 99/51259 A3 | 10/1999 |
| WO | WO 99/56755 A1 | 11/1999 |
| WO | WO 99/62923 A2 | 12/1999 |
| WO | WO 99/62923 A3 | 12/1999 |
| WO | WO 00/06588 A1 | 2/2000 |
| WO | WO 00/16804 A1 | 3/2000 |
| WO | WO 00/21556 A1 | 4/2000 |
| WO | WO 00/62802 A2 | 10/2000 |
| WO | WO 00/62802 A3 | 10/2000 |
| WO | WO 00/67023 A1 | 11/2000 |
| WO | WO 01/02007 A1 | 1/2001 |
| WO | WO 01/12223 A2 | 2/2001 |
| WO | WO 01/55341 A2 | 8/2001 |
| WO | WO 01/55341 A3 | 8/2001 |
| WO | WO 01/68077 A2 | 9/2001 |
| WO | WO 01/68077 A3 | 9/2001 |
| WO | WO-01/68078 A2 | 9/2001 |
| WO | WO-01/68078 A3 | 9/2001 |
| WO | WO 01/68103 A2 | 9/2001 |
| WO | WO 01/68103 A3 | 9/2001 |
| WO | WO 01/68116 A2 | 9/2001 |
| WO | WO 01/68116 A3 | 9/2001 |
| WO | WO 01/68117 A2 | 9/2001 |
| WO | WO 01/68117 A3 | 9/2001 |
| WO | WO 01/68143 A2 | 9/2001 |
| WO | WO 01/68143 A3 | 9/2001 |
| WO | WO 01/68144 A2 | 9/2001 |
| WO | WO 01/68144 A3 | 9/2001 |
| WO | WO 01/76642 A1 | 10/2001 |

OTHER PUBLICATIONS

Fearon et al. A minimal human immunostimulatory CpG motif that potently induces IFN-gamma and IFN-alpha production. Eur J. Immunol., Aug. 2003, vol. 33, No. 8, 2114-2122.*

Agrawal, S. and Kandinalla, E.R. (2002). "Medicinal Chemistry and Therapeutic Potential of CpG DNA," *Trends in Molecular Medicine* 8(3):114-121.

Ausubel Frederick M. et al., eds. (1995). *Current Protocols in Molecular Biology.* vol. 1, John Wiley & Sons, Inc.: pp. iii-xii (Table of Contents).

Ballas, Zuhair et al. (1996). "Induction of NK Activity in Murine and Human Cells by CpG Motifs in Oligodeoxynucleotides and Bacterial DNA" *J. Immunol.* 157:1840-1845.

Beaucage, Serge L. (1993). "Oligodeoxyribonucleotide Synthesis" vol. 20 Chapter 3 *in Protocols for Oligonucleotides and Analogs, Synthesis and Properties*, Agrawal (ed.), Humana Press: Totowa, NJ. pp. 33-61.

Branda, Richard F. et al. (1993). "Immune Stimulation by an Antisense Oligomer Complementary to the Rev Gene of HIV-1" *Biochem. Pharmacol.* 45(10):2037-2043.

Branda, Richard F. et al. (1996). "Amplification of Antibody Production by Phosphorothioate Oligodeoxynucleotides" *J. Lab. Clin. Med.* 128(3):329-338.

Braun, Ralph P. and Lee, Jeremy S. (1988). "Immunogenic Duplex Nucleic Acids are Nuclease Resistant" J. Immunol. 141(6):2084-2089.

Brazolot Millan, Cynthia L. et al. (1998). "CpG DNA can Induce Strong Th1 Humoral and Cell-Mediated Immune Responses Against Hepatitis B Surface Antigen in Young Mice" *Proc. Natl. Acad. Sci. USA* 95:15553-15558.

Broide, David et al. (1998). "Immunostimulatory DNA Sequences Inhibit IL-5, Eosinophilic Inflammation, and Airway Hyper-responsiveness in Mice" *J. Immunol.* 161:7054-7062.

Broide, David and Raz, Eyal (1999). "DNA-Based Immunization for Asthma" *Int. Arch. Allergy Immunol.* 118:453-456.

Carson, Dennis A. and Raz, Eyal (1997). "Oligonucleotide Adjuvants for T Helper 1 (Th1)-Specific Vaccination" *J. Exp. Med.* 186(10):1621-1622.

Chace, Jacqueline H. et al. (1997). "Bacterial DNA-Induced NK Cell IFN-Gamma Production is Dependent on Macrophage Secretion of IL-12" *Clin. Immunol. and Immunopathol.* 84(2):185-193.

Chaturvedi, Surendra et al. (1996). "Stabilization of Triple-Stranded Oligonucleotide Complexes: Use of Probes Containing Alternating Phosphodiester and Stereo-Uniform Cationic Phosphoramidate Linkages" *Nucleic Acids Res.* 24(12):2318-2323.

Chu, Rose S. et al. (1997). "CpG Oligodeoxynucleotides Act as Adjuvants that Switch on T Helper 1 (Th1) Immunity" *J. Exp. Med.* 186(10):1623-1631.

Coligan, John E. et al., eds. (1998). *Current Protocols in Immunology* vol. 1, John Wiley & Sons, Inc: pp. 1-9 (Table of Contents).

Cowdery, John S. et al. (1996). "Bacterial DNA Induces NK Cells to Produce IFN-Gamma in Vivo and Increases the Toxicity of Lipopolysaccharides" *J. Immunol.* 156:4570-4575.

Dartmann et al. (1986). "The Nucleotide Sequence and Genome Organization of Human Papilloma Virus Type 11," *Virology* 151:124-130.

Davis, H. et al. (1998). "CpG DNA is a Potent Enhancer of Specific Immunity in Mice Immunized with Recombinant Hepatitis B Surface Antigen," *Journal of Immunology* 160(2):870-876.

Dolin. (1985). "Antiviral Chemotherapy and Chemoprophylaxis," *Science* 227:1296-1303.

Elkins, Karen L. et al. (1999). "Bacterial DNA Containing CpG Motifs Stimulates Lymphocyte-Dependent Protection of Mice Against Lethal Infection with Intracellular Bacteria" *J. Immunol.* 162:2291-2298.

Freshney, R.I., ed. (1987). *Animal Cell Culture: A Practical Approach.* IRL Press: pp. vii-xii (Table of Contents).

Gait, M. J., ed. (1984). *Oligonucleotide Synthesis: A Practical Approach* IRL Press: pp. vii-xii (Table of Contents).

Galibert et al. (1979). "Nucleotide sequence of the hepatitis B virus genome (subtype ayw) cloned in *E. coli*" Nature 281:646-650.

Gao, Hetian et al. (1995). "Circulation of Oligonucleotides by Disulfide Bridge Formation" *Nucleic Acids Res.* 23(11):2025-2029.

Gene Characterization Kits. (1988). Stratagene 1988 Catalog:39.

Godard, Gérard et al. (1995). "Antisense Effects of Cholesterol-Oligodeoxynucleotide Conjugates Associated with Poly(Alkylcyanoacrylate) Nanoparticles" *Eur. J. Biochem.* 232:404-410.

Gramzinski, Robert A. et al. (1998). "Immune Response to a Hepatitis B DNA Vaccine in Aotus Monkeys: a Comparison of Vaccine Formulation, Route, and Method of Administration" *Mol. Med.* 4:109-118.

Horner, Anthony A. et al. (1998). "Immunostimulatory DNA is a Potent Mucosal Adjuvant" *Cell. Immunol.* 190:77-82.

Jäger, Alfred et al. (1988). "Oligonucleotide N-Alkylphosphoramidates: Synthesis and Binding to Polynucleotides" *Biochem.* 27(19):7237-7246.

Jakob, Thilo et al. (1998). "Activation of Cutaneous Dendritic Cells by CpG-Containing Oligodeoxynucleotides: a Role for Dendritic Cells in the Augmentation of Th1 Responses by Immunostimulatory DNA" *J. Immunol.* 161:3042-3049.

Kataoka, Tetsuro et al. (1992). "Antitumor Activity of Synthetic Oligonucleotides with Sequences from cDNA Encoding Proteins of Mycobacterium Bovis BCG" *Jpn. J. Cancer Res.* 83:244-247.

Kimura, Yoshimitsu et al. (1994). "Binding of Oligoguanylate to Scavenger Receptors is Required for Oligonucleotides to Augment NK Cell Activity and Induce IFN" *J. Biochem.* (Tokyo) 116(5):991-994.

Kline, J. N. et al. (1997). "Immune Redirection by CpG Oligonucleotides Conversion of a Th2 Response to a Th1 Response in a Murine Model of Asthma" *J. Invest. Med.* 45(3):282A.

Klinman, Dennis M. et al. (1996). "CpG Motifs Present in Bacterial DNA Rapidly Induce Lymphocytes to Secrete Interleukin 6, Interleukin 12, and Interferon Gamma" *Proc. Natl. Acad. Sci. USA* 93:2879-2883.

Klinman, Dennis M. et al. (1997). "Contribution of CpG Motifs to the Immunogenicity of DNA Vaccines" *J. Immunol.* 158:3635-3639.

Kmiec. (1999). "Gene Therapy," *American Scientist* 87:240-247.

Kovarik, Jiri et al. (1999). "CpG Oligodeoxynucleotides can Circumvent the Th2 Polarization of Neonatal Responses to Vaccines but May Fail to Fully Redirect Th2 Responses Established by Neonatal Priming" *J. Immunol.* 162:1611-1617.

Krieg, Arthur M. et al. (1989). "A Role for Endogenous Retroviral Sequences in the Regulation of Lymphocyte Activation" *J. Immunol.* 143(8):2448-2451.

Krieg, Arthur M. et al. (1995). "CpG Motifs in Bacterial DNA Trigger Direct B-Cell Activation" *Nature* 374:546-549.

Krieg, Arthur M. (1996). "Lymphocyte Activation by CpG Dinucleotide Motifs in Prokaryotic DNA" *Trends Microbiol.* 4(2):73-77.

Krieg, Arthur M. et al. (1996). "Oligodeoxynucleotide Modifications Determine the Magnitude of B Cell Stimulation by CpG Motifs" *Antisense Nucleic Acid Drug Dev.* 6:133-139.

Krieg, Arthur M. (1998). "Leukocyte Stimulation by Oligodeoxynucleotides" Chapter 24 *in Applied Antisense Oligonucleotide Technology* C.A. Stein et al. eds. Wiley-Liss, Inc.: pp. 431-448.

Krieg, Arthur M. et al. (1998a). "The Role of CpG Dinucleotides in DNA Vaccines" *Trends Microbiol.* 6(1):23-27.

Krieg, Arthur M. et al. (1998b). "CpG DNA Induces Sustained IL-12 Expression in Vivo and Resistance to Listeria Monocytogenes Challenge" *J. Immunol.* 161:2428-2434.

Krieg, Arthur M. et al. (1998c). "Sequence Motifs in Adenoviral DNA Block Immune Activation by Stimulatory CpG Motifs" *Proc. Natl. Acad. Sci. USA* 95:12631-12636.

Krieg, Arthur M. (1999). "CpG DNA: a Novel Immunomodulator" *Trends Microbiol.* 7(2):64-65.

Krieg. (1999). "Direct Immunologic Activities of CpG DNA and Implications for Gene Therapy," *The Journal of Gene Medicine* 1:56-63.

Latimer, Laura J. P. et al. (1995). "Specificity of Monoclonal Antibodies Produced Against Phosphorothioate and Ribo Modified DNAs" *Mol. Immunol.* 32(14/15):1057-1064.

Leclerc, Claude et al. (1997). "The Preferential Induction of a Th1 Immune Response by DNA-Based Immunization is Mediated by the Immunostimulatory Effect of Plasmid DNA" *Cell. Immunol.* 179:97-106.

Liang, Hua et al. (1996). "Activation of Human B Cells by Phosphorothioate Oligodeoxynucleotides" *J. Clin. Invest.* 98(5):1119-1129.

Lipford, Grayson B. et al. (1997a). "CpG-Containing Synthetic Oligonucleotides Promote B and Cytotoxic T Cell Responses to Protein Antigen: A New Class of Vaccine Adjuvants" *Eur. J. Immunol.* 27:2340-2344.

Lipford, Grayson B. et al. (1997b). "Immunostimulatory DNA: Sequence-Dependent Production of Potentially Harmful or Useful Cytokines" *Eur. J. Immunol.* 27:3420-3426.

Liu, Hsin-Ming et al. (1998). "Immunostimulatory CpG Oligodeoxynucleotides Enhance the Immune Response to Vaccine Strategies Involving Granulocyte-Macrophage Colony-Stimulating Factor" *Blood* 92(10):3730-3736.

Macfarlane, D.E. et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step" *Immunology* 91:586-593.

Manzel, Lori and MacFarlane, Donald E. (1999). "Lack of Immune Stimulation by Immobilized CpG-Oligodeoxynucleotide" *Antisense Nucl. Acid Drug Dev.* 9:459-464.

Marshalls. (1995). "Gene Therapy's Growing Pains," *Science* 269:1050-1055.

Martin-Orozco, Elena et al. (1999). "Enhancement of Antigen-Presenting Cell Surface Molecules Involved in Cognate Interactions by Immunostimulatory DNA Sequences" *Int. Immunol.* 11(7):1111-1118.

Masseyeff, René F., ed. (1993). *Methods of Immunological Analysis. vol. 1: Fundamentals*. Verlagsgesellschaft mbH, D-6940: Weinheim, Germany: pp. xi-xxii (Table of Contents).

Matteucci (1997) "Oligonucleotide Analogs:an Overview" in *Oligonucleotides as Therapeutic Agents*, (D.J. Chadwick and G. Cardew, ed.) John Wiley and Sons, New York, NY: pp. 5-18.

McCluskie, Michael J. and Davis, Heather L. (1998). "CpG DNA is a Potent Enhancer of Systemic and Mucosal Immune Responses Against Hepatitis B Surface Antigen with Intranasal Administration to Mice" *J. Immunol.* 161:4463-4466.

Miller, Jeffrey H. and Calos, Michele B., eds. (1987). "Gene Transfer Vectors for Mammalian Cells" *in Current Communications in Molecular Biology*. Cold Spring Harbor Laboratory: pp. vii-ix (Table of Contents).

Miller, Paul S. et al. (1971). "Syntheses and Properties of Adenine and Thymine Nucleoside Alkyl Phosphotriesters, the Neutral Analogs of Dinucleoside Monophosphates" *JACS* 93(24):6657-6665.

Mojcik, Christopher F. et al. (1993). "Administration of a Phosphorothioate Oligonucleotide Antisense to Murine Endogenous Retroviral MCF *Env* Causes Immune Effects in Vivo in a Sequence-Specific Manner" *Clin. Immunol. and Immunopathol.* 67(2):130-136.

Moldoveanu, Zina et al. (1998). "CpG DNA, a Novel Immune Enhancer for Systemic and Mucosal Immunization with Influenza Virus" *Vaccine* 16(11/12):1216-1224.

Mountain. (2000). "Gene Therapy: The First Decade," *TIBTECH* 18:119-128.

Mullis, Kary B. et al., eds. (1994) *PCR: The Polymerase Chain Reaction*. Birkhäuser: pp. xv-xvii (Table of Contents).

Nelson, Jeffrey S. et al. (1997). "N3'→P5' Oligodeoxyribonucleotide Phosphoramidates: A New Method of Synthesis Based on a Phosphoramidite Amino-Exchange Reaction" *J. Org. Chem.* 62:7278-7287.

Orkin et al. (1995). *Report and Recommendations of the Panel to Assess the NIH Investment in Research on Gene Therapy*.

Peyrottes, Suzanne et al. (1996). "Oligodeoxynucleoside Phosphoramidates (P-NH2): Synthesis and Thermal Stability of Duplexes with DNA and RNA Targets" *Nucleic Acids Res.* 24(10):1841-1848.

Pisetsky, David S. and Reich, Charles F. (1994). "Stimulation of Murine Lymphocyte Proliferation by a Phosphorothioate Oligonucleotide with Antisense Activity for Herpes Simplex Virus" *Life Sci.* 54(2):101-107.

Pisetsky, David S. et al. (1995). "Immunological Properties of Bacterial DNA" *Ann. N.Y. Acad. Sci.* 772:152-163.

Pisetsky, David S. (1996a). "The Immunologic Properties of DNA" *J. Immunol.* 156(2):421-423.

Pisetsky, David S. (1996b). "Immune Activation by Bacterial DNA: a New Genetic Code" *Immunity* 5:303-310.

Raz, Eyal et al. (1994). "Intradermal Gene Immunization: the Possible Role of DNA Uptake in the Induction of Cellular Immunity to Viruses" *Proc. Natl. Acad. Sci. USA* 91:9519-9523.

Raz, Eyal et al. (1996). "Preferential Induction of a Th1 Immune Response and Inhibition of Specific IgE Antibody Formation by Plasmid DNA Immunization" *Proc. Natl. Acad. Sci. USA* 93:5141-5145.

Redford, Thomas W. et al. (1998). "Cyclosporin A Enhances IL-12 Production by CpG Motifs in Bacterial DNA and Synthetic Oligodeoxynucleotides" *J. Immunol.* 161:3930-3935.

Romagnani, Sergio (2000). "T-Cell Subsets (Th1 versus Th2)" *Ann. Allergy Asthma Immunol.* 85(1):9-18.

Roman, Mark et al. (1997). "Immunostimulatory DNA Sequences Function as T Helper-1-Promoting Adjuvants" *Nature Med.* 3(8):849-854.

Romano et al. (2000). "Latest Developments in Gene Transfer Technology: Achievements, Perspectives, and Controversies over Therapeutic Applications," *Stem Cell* 18:19-39.

Sambrook, J. et al., eds. (1989). *Molecular Cloning: A Laboratory Manual*, Second Edition, Cold Spring Harbor Laboratory Press: pp. x-xxxviii (Table of Contents).

Sato, Yukio et al. (1996). "Immunostimulatory DNA Sequences Necessary for Effective Intradermal Gene Immunization" *Science* 273:352-354.

Schacht, Etienne et al. (1996). "Biomedical Applications of Degradable Polyphosphazenes" *Biotechnol. Bioeng.* 52:102-108.

Schultz, Ronald G. and Gryaznov, Sergei M. (1996). "Oligo-2'-Fluoro-2'-Deoxynucleotide N3'→P5 Phosphoramidates: Synthesis and Properties" *Nucleic Acids Res.* 24(15):2966-2973.

Schwartz, David A. et al. (1997). "CpG Motifs in Bacterial DNA Cause Inflammation in the Lower Respiratory Tract" *J. Clin. Invest.* 100(1):68-73.

Shigeta, S. (1998). "Approaches to Antiviral Chemotherapy for Acute Respiratory Infections," *Antiviral Chemistry & Chemotherapy* 9:93-107.

Shimada, Shizuo et al. (1986). "In Vivo Augmentation of Natural Killer Cell Activity with a Deoxyribonucleic Acid Fraction of BCG" *Jpn. J. Cancer Res.* 77:808-816.

Sonehara, Kazuhiko et al. (1996). "Hexamer Palindromic Oligonucleotides with 5'-CG-3' Motif(s) Induce Production of Interferon" *J. Interferon and Cytokine Res.* 16:799-803.

Sparwasser, Tim et al. (1997). "Macrophages Sense Pathogens Via DNA Motifs: Induction of Tumor Necrosis Factor-Alpha-Mediated Shock" *Eur. J. Immunol.* 27:1671-1679.

Spiegelberg, H.L. et al. (1998). "Inhibition of IgE Formation and Allergic Inflammation by Allergen Gene Immunization and by CpG Motif Immunostimulatory Oligodeoxynucleotides" *Allergy* 53:93-97.

Spiegelberg, Hans L. et al. (1999). "Inhibition of Allergic Inflammation in the Lung by Plasmid DNA Allergen Immunization" *Pediatr. Pulmonol.* Suppl. 18:118-121.

Stacey, Katryn J. et al. (1996). "Macrophages Ingest and are Activated by Bacterial DNA" *J. Immunol.* 157(5):2116-2122.

Stein, C.A. and Krieg, Arthur (1997). "Non-Antisense Effects of Oligodeoxynucleotides" Chapter 11 in *Antisense Technology* Lichtenstein, C. and Nellen, W. eds., IRL Press: pp. 241-264.

Stirchak, Eugene P. et al. (1989). "Uncharged Stereoregular Nucleic Acid Analogs: 2. Morpholino Nucleoside Oligomers with Carbamate Internucleoside Linkages" *Nucleic Acids Res.* 17(15):6129-6141.

Sundaram et al. (1998). "Intracutaneous Vaccination of Rabbitis with the E6 Gene of Cottontail Rabbit Papillomavirus Provides Partial Protetion Against Virus Challenge," *Vaccine* 16(6):613-623.

Tokunaga, Tohru et al. (1992). "Synthetic Oligonucleotides with Particular Base Sequences from the cDNA Encoding Proteins of Mycobacterium Bovis BCG Induce Interferons and Activate Natural Killer Cells" *Microbiol. Immunol.* 36(1):55-66.

Tokunaga et al. (1999). "How BCG Led to the Discovery of Immunotimulatory DNA," *Jpn. J. Infec. Dis.* 52:1-11.

Van Nest, G. et al. (1999). "An Immunostimulatory Oligonucleotide (ISS ODN) Enhances Immune Responses to HBV Vaccine in a Variety of Animal Species Including Primates," *Abstracts of the Interscience Conference of Antimicrobial Agents* p. 374, abstract No. 679.

Verma et al. (1997). "Gene Therapy—Promises, Problems, and Prospects," *Nature* 389:239-242.

Wang, Shaohui and Kool, Eric T. (1994). "Circular RNA Oligonucleotides. Synthesis, Nucleic Acid Binding Properties, and a Comparison with Circular DNAs" *Nucleic Acids Res.* 22(12):2326-2333.

Warner, B.D. et al. (1984). "Construction and Evaluation of an Instrument for the Automated Synthesis of Oligodeoxyribonucleotides" *DNA* 3(5):401-411.

Weeratna, Risini et al. (1998). "Reduction of Antigen Expression from DNA Vaccines by Coadministered Oligodeoxynucleotides" *Antisense and Nucleic Acid Drug Development* 8:351-356.

Weiner, George J. et al. (1997). "Immunostimulatory Oligodeoxynucleotides Containing the CpG Motif are Effective as Immune Adjuvants in Tumor Antigen Immunization" *Proc. Natl. Acad. Sci. USA* 94:10833-10837.

Weir, D.M., ed., *Handbook of Experimental Immunology in Four Volumes* "vol. 4: Applications of Immunological Methods in Biomedical Sciences" Blackwell Scientific Publications: pp. v-x (Table of Contents).

Wild, David, ed., (1994). *The Immunoassay Handbook*, Stockton Press: pp. v-xvi (Table of Contents).

Wooldridge, James E. et al. (1997). "Immunostimulatory Oligodeoxynucleotides Containing CpG Motifs Enhance the Efficacy of Monoclonal Antibody Therapy of Lymphoma" *Blood* 89(8):2994-2998.

Yamamoto, Saburo et al. (1992). "Unique Palindromic Sequences in Synthetic Oligonucleotides are Required to Induce IFN [correction of INF] and Augment IFN-Mediated [correction of INF] Natural Killer Activity" *J. Immunol.* 148(12):4072-4076.

Yamamoto, Toshiko et al. (1994a). "Ability of Oligonucleotides with Certain Palindromes to Induce Interferon Production and Augment Natural Killer Cell Activity is Associated with Their Base Length" *Antisense Research and Development* 4:119-122.

Yamamoto, Toshiko et al. (1994b). "Synthetic Oligonucleotides with Certain Palindromes Stimulate Interferon Production of Human Peripheral Blood Lymphocytes in Vitro" *Jpn. J. Cancer Res.* 85:775-779.

Yi, Ae-Kyung et al. (1996). "IFN-Gamma Promotes IL-6 and IgM Secretion in Response to CpG Motifs in Bacterial DNA and Oligodeoxynucleotides" *J. Immunol.* 156(2):558-564.

Yi, Ae-Kyung and Krieg, Arthur M. (1998a). "CpG DNA Rescue from Anti-IgM-Induced WEHI-231 B Lymphoma Apoptosis Via Modulation of I Kappa B Alpha and I Kappa B Beta and Sustained Activation of Nuclear Factor-Kappa B/c-Rel" *J. Immunol.* 160(3):1240-1245.

Yi, Ae-Kyung et al.(1998b). "CpG Motifs in Bacterial DNA Activate Leukocytes Through the pH-Dependent Generation of Reactive Oxygen Species" *J. Immunol.* 160(10):4755-4761.

Yi, Ae-Kyung et al. (1998c). "CpG Oligodeoxyribonucleotides Rescue Mature Spleen B Cells from Spontaneous Apoptosis and Promote Cell Cycle Entry" *J. Immunol.* 160(12):5898-5906.

Yi, Ae-Kyung and Krieg, Arthur M. (1998d). "Cutting Edge: Rapid Induction of Mitogen-Activated Protein Kinases by Immune Stimulatory CpG DNA" *J. Immunol.* 161(9):4493-4497.

Zhao, Qiuyan et al. (1996). "Effect of Different Chemically Modified Oligodeoxynucleotides on Immune Stimulation" *Biochem. Pharmacol.* 51(2):173-182.

Zimmermann, Stefan et al. (1998). "CpG Oligodeoxynucleotides Trigger Protective and Curative Th1 Responses in Lethal Murine Leishmaniasis" *J. Immunol.* 160(8):3627-3630.

Zon, Gerald (1993). "Oligonucleoside Phosphorothioates" Chapter 8 in *Protocols for Oligonucleotides and Analogs, Synthesis and Properties*, Agrawal (ed.), Humana Press: pp. 165-189.

Fearon, K. (2003). "A Minimal Human Immunostimulatory CpG Motif That Potently Induces IFN-Gamma and IFN-Alpha Production," *Eur. J. Immunol.* 33:2114-2212.

Hartmann, G. et al. (2000). "Mechanism and Function of a Newly Identified CpG DNA Motif in Human Primary B Cells," *J. Immunology* 164:944-952.

Marshall, J.D. (2003), "Novel Chimeric Immunomodulatory Compounds Containing Short CpG Oligodeoxyribonucleotides Have Differential Activities in Human Cells," *Nucleic Acids Research* 31(17):5122-5133.

Marshall, J.D. (2005). "Superior Activity of the Type C Class of ISS in Vitro and in Vivo Across Multiple Species," *DNA and Cell Bio.* 24(2):63-72.

Agrawal, S. et al. (Mar. 2002). "Medicinal Chemistry and Therapeutic Potential of CpG DNA," *Trends in Molecular Medicine* 8(3):114-121.

Broide, D. et al. (Feb.-Apr. 1999). "DNA-Based Immunization for Asthma" *International. Archives of Allergy Immunology*, 118(2-4):453-456.

Coley Pharmaceutical Group, Inc. (Oct. 30, 2002). "Coley Pharmaceutical Group Identifies New Class of CpG Oligonucleotides," Press Release located at <http://www.coleypharma.com/coley/pr_1036000898.html>, last visited on Apr. 11, 2007, two pages.

Coley Pharmaceutical Group, Inc. (Sep. 27, 2005). "Coley Pharmaceutical Group Initiates Second Phase lb Clinical Study of Actilon™ for Treatment of HCV," Press Release located at <http://www.coleypharma.com/coley/pr_1127805994.html>, last visited on Apr. 11, 2007, two pages.

Coley Pharmaceutical Group, Inc. (Jan. 22, 2007). "Coley Pharmaceutical Group Updates Hepatitis C Drug Development Strategy," Press Release located at <http://www.coleypharma.com/coley/pr_20070122.html>, last visited on Apr. 11, 2007, three pages.

Elkins, K.L. et al. (Feb. 1999). "Bacterial DNA Containing CpG Motifs Stimulates Lymphocyte-Dependent Protection of Mice Against Lethal Infection with Intracellular Bacteria" *Journal of Immunology*. 162(4):2291-2298.

Kanzler H. et al. (May 2007, e-published May 3, 2007). "Therapeutic Targeting of Innate Immunity with Toll-like Receptor Agonists and Antagonists," *Nature Medicine* 13(5): 552-559.

Kmiec E.B. (May-Jun. 1999). "Gene Therapy," *American Scientist* 87(3):240-247.

Kovarik, J. et al. (Feb. 1, 1999). "CpG Oligodeoxynucleotides can Circumvent the Th2 Polarization of Neonatal Responses to Vaccines but May Fail to Fully Redirect Th2 Responses Established by Neonatal Priming" *Journal of Immunology* 162(3):1611-1617.

Krieg, A.M. et al. (Apr. 2002). "CpG Motifs in Bacterial DNA and Their Immune Effects," *Annual Review of Immunology*. 20:709-760.

Krieg, A.M. (Feb. 1999). "CpG DNA: a Novel Immunomodulator" *Trends in Microbiology* 7(2):64-65.

Krieg, A.M. (Jan.-Feb. 1999). "Direct Immunologic Activities of CpG DNA and Implications for Gene Therapy," *The Journal of Gene Medicine* 1(1):56-63.

Manzel, L. et al. (Oct. 1999). "Lack of Immune Stimulation by Immobilized CpG-Oligodeoxynucleotide" *Antisense and Nucleic Acid Drug Development* 9(5):459-464.

Martin-Orozco, E. et al. (Jul. 1999). "Enhancement of Antigen-Presenting Cell Surface Molecules Involved in Cognate Interactions by Immunostimulatory DNA Sequences" *International Immunology* 11(7):1111-1118.

McHutchinson, J.G. et al. (Apr. 2006). "Early Viral Response to New HCV Drug CPG 10101 Toll-Receptor Antagonist, in Combination with Pegylated Interferon and/or Ribavirin, in Chronic HCV Genotype 1 Infected Patients with Prior Relapse Response," *41st Meeting of the European Association for the Study of Liver Diseases*, Vienna, Austria, Apr. 26-30, 2006, located at <http://www.natap.org/2006/EASL/EASL_24.htm>, last visited on Apr. 11, 2007, eight pages.

McHutchinson, J.G. et al. (Apr. 2006). "Randomized, Placebo-Controlled, Dose-Escalation Trial of New HCV Drug CPG 10101 Toll-Receptor Antagonist in Patients with Chronic Hepatitis C Virus," *41st Meeting of the European Association for the Study of Liver Diseases*, Vienna, Austria, Apr. 26-30, 2006, located at <http://www.natap.org/2006/EASL/EASL_23.htm>, last visited on Apr. 11, 2007, eleven pages.

Mountain A. (Mar. 2000). "Gene Therapy: The First Decade," *Trends in Biotechnology* 18(3):119-128.

Mutwiri, G. et al. (Feb. 2003). "Biological Activity of Immunostimulatory CpG DNA Motifs in Domestic Animals," *Veterinary Immunology and Immunopathology* 91:89-103.

Romagnani, S. (Jul. 2000). "T-Cell Subsets (Th1 versus Th2)" *Annals of Allergy, Asthma, and Immunology* 85(1):9-18.

Romano S. et al. (Jan. 2000). "Latest Developments in Gene Transfer Technology: Achievements, Perspectives, and Controversies over Therapeutic Applications," *Stem Cells* 18(1):19-39.

Spiegelberg, H.L. et al. (Oct. 1999). "Inhibition of Allergic Inflammation in the Lung by Plasmid DNA Allergen Immunization" *Pediatric Pulmonology*. Supplemental 18:118-121.

Tokunaga et al. (Feb. 1999). "How BCG Led to the Discovery of Immunotimulatory DNA," *Japanese Journal of Infectious Diseases* 52(1):1-11.

Van Nest, G. et al. (Feb. 1999). "An Immunostimulatory Oligonucleotide (ISS ODN) Enhances Immune Responses to HBV Vaccine in a Variety of Animal Species Including Primates," *Abstracts of the Interscience Conference of Antimicrobial Agents* p. 374, abstract No. 679.

Weir, D.M. (May 1986). *Handbook of Experimental Immunology in Four Volumes*: vol. 4: *Applications of Immunological Methods in Biomedical Sciences*, Blackwell Scientific Publications: Edinburgh, Scotland, UK pp. v-x (Table of Contents Only).

Yamamoto, S. et al. (Feb. 2000). "Oligodeoxyribonucleotides With 5'-ACGT-3' or 5'-TCGA-3' Sequence Induce Production of Interferons," *Current Topics in Microbiology and Immunology* 247:23-39.

Aoki, N. et al. (2004). "Use of Cytokines in Infection," *Expert Opin. Emerg. Drugs* 9(2):223-236.

Hartmann, G. et al. (2000). "Delineation of a CpG Phosphorothioate Oligodeoxynucleotide for Activating Primate Immune Responses In Vitro and In Vivo," *J. Immunol.* 164(3):1617-1624.

Infante-Duarte, C. et al. (1999). "Th1/Th2 Balance in Infection," *Springer Seminars in Immunopathology* 21(3):317-338.

International Search Report mailed Jun. 17, 2002 for PCT Application No. PCT/US01/07839, filed Mar. 12, 2001, 4 pages.

International Search Report mailed Jun. 17, 2002 for PCT Application No. PCT/US01/07840 filed Mar. 12, 2001, 4 pages.

International Search Report mailed Jun. 17, 2002 for PCT Application No. PCT/US01/07842 filed Mar. 12, 2001, 4 pages.

International Search Report mailed Jun. 17, 2002 for PCT Application No. PCT/US01/07931 filed Mar. 12, 2001, 5 pages.

International Search Report mailed Jun. 18, 2002 for PCT Application No. PCT/US01/07841 filed Mar. 12, 2001, 4 pages.

Krieg, A.M. (Aug. 1996). "An Innate Immune Defense Mechanism Based on the Recognition of CpG Motifs in Microbial DNA," *J. Lab. Clin. Med.* 128(2):128-133.

Krieg, A.M. (2000). "The Role of CpG Motifs in Innate Immunity," *Current Opinion in Immunology* 12:35-43.

* cited by examiner

METHODS OF SUPPRESSING HEPATITIS VIRUS INFECTION USING IMMUNOMODULATORY POLYNUCLEOTIDE SEQUENCES

CROSS-REFERENCE TO RELATED APPLICATIONS

The present application is a continuation of U.S. patent application Ser. No. 09/802,370, filed Mar. 9, 2001, abandoned which in turn claims the priority benefit of U.S. Provisional application 60/188,301, filed Mar. 10, 2000, each of which is hereby incorporated herein by reference in its entirety.

TECHNICAL FIELD

This invention is in the field of immunomodulatory polynucleotides, more particularly their use in ameliorating or preventing hepatitis viral infection and/or symptoms of hepatitis virus infection.

BACKGROUND ART

Hepatitis is a generic term for disease involving inflammation of the liver. A variety of agents can cause hepatitis, including viruses, drugs, toxins, and autoimmune disorders. Additionally, hepatitis can arise secondary to non liver-related disorders. Viral infection is the most common cause of hepatitis.

At least 8 different hepatitis viruses are believed to exist, and include the A, B, C, D, E, F, G and cryptogenic hepatitis viruses. The hepatitis viruses are spread through a number of different virus families. Of these viruses, hepatitis B virus (HBV, a hepadnavirus) and hepatitis C virus (HCV, a flavivirus) pose the greatest public health problem in industrialized countries. Both hepatitis B and C are bloodborne diseases, although both viruses may also be transmitted perinatally and via sexual contact.

Hepatitis B and C can each give rise to acute and chronic infections. A relatively low level of mortality is due to acute B and C hepatitis (primarily due to fulminant hepatitis). However, the chronic forms of each disease pose significant medical issues. HBV is the most prevalent chronic infectious disease in the world, and poses a substantially larger perinatal transmission risk than HCV, with 90% of children born to HBV-infected mothers becoming lifelong carriers. HCV is currently the leading cause of liver transplants in the United States.

Only about half of HBV infections, and even fewer HCV infections, are symptomatic in the acute phase, which typically presents with symptoms such as jaundice, fatigue, abdominal pain and/or loss of appetite. Subclinical infections can be detected using diagnostic testing for viral antigens and/or DNA.

The vast majority (95-98%) of adults infected with HBV resolve their disease and experience no further ill effects, although newborns are at substantial risk of developing a chronic infection, with approximately 80-90% of perinatally infected individuals developing chronic disease. Chronic HBV infection is typically asymptomatic, although some symptoms of acute hepatitis B may be present. The long term sequelae of chronic HBV infection include liver fibrosis/cirrhosis, liver cancer, liver failure and death.

Chronic HBV infection is a substantial public health issue in Asia, where comparatively large percentages of the population are chronically infected with HBV. Mirroring these high rates of chronic infection are rates of hepatocellular carcinoma (HCC), a liver cancer associated with chronic HBV infection.

In the U.S., acute HCV infections are substantially less common than acute HBV infections, by a factor of approximately ten. However, due to the substantially greater risk of progression to chronic infection ($\geq 85\%$), the prevalence of chronic HCV infection is two to three times greater than that for chronic HBV infection. Additionally, HCV infection carries a much greater risk of the development of chronic liver disease and liver failure.

Although HBV and HCV are very different viruses, treatments for chronic infections with the two viruses are virtually identical. Currently available treatments for chronic hepatitis B and C infection are limited to interferons. Interferon $\alpha$-2a, interferon $\alpha$-2b and interferon alfacon-1 (a recombinant, non-naturally occurring interferon 1 variant) are currently used for the treatment of chronic hepatitis virus infection, although "combination" therapy with ribavirin (an anti-viral drug) and interferon $\alpha$-2b has also been approved for the treatment of chronic hepatitis C. However, these drugs require frequent administration and are associated with a large number of side effects, including "flu-like" symptoms (e.g., fatigue, fever, myalgia), leukopenia, thrombocytopenia, nausea, vomiting, and arthralgia. One rare complication of interferon administration is hepatotoxicity, which can be fatal. Unfortunately, only about 40% of patients show any improvement with interferon treatment, and may relapse after treatment is completed.

Currently, a number of new drugs are being developed for treatment of chronic HBV infection, including interferon $\beta$, interferon $\gamma$, interleukin 2, thymosin, acyclovir, lamivudine (3TC), and granulocyte colony factor. These drugs typically require long courses of administration, and most are accompanied by significant side effects.

Administration of certain DNA sequences, generally known as immunostimulatory sequences or "ISS," induces an immune response with a Th1-type bias as indicated by secretion of Th1-associated cytokines. The Th1 subset of helper cells is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) $\beta$-galactosidase ($\beta$-Gal) in saline or in the adjuvant alum responded by producing specific IgG1 and IgE antibodies, and CD4$^+$ cells that secreted IL-4 and IL-5, but not IFN-$\gamma$, demonstrating that the T cells were predominantly of the Th2 subset. However, mice injected intradermally (or with a tyne skin scratch applicator) with plasmid DNA (in saline) encoding $\beta$-Gal and containing an ISS responded by producing IgG2a antibodies and CD4$^+$ cells that secreted IFN-$\gamma$, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4⁺ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem.* (Tokyo) 116:991-994; Krieg et al. (1995) *Nature* 374: 546-549; Pisetsky et al. (1995) *Ann. N.Y. Acad. Sci.* 772:152-163; Pisetsky (1996a) *J. Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156: 558-564; Krieg (1996) *Trends Microbiol.* 4(2):73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996) *J. Lab. Clin. Med.* 128:329-338; Sonehara et al. (1996) *J. Interferon and Cytokine Res.* 16:799-803; Klinman et al. (1997) *J. Immunol.* 158:3635-3639; Sparwasser et al. (1997) *Eur. J. Immunol.* 27:1671-1679; Roman et al. (1997); Carson et al. (1997) *J. Exp. Med.* 186:1621-1622; Chace et al. (1997) *Clin. Immunol. and Immunopathol.* 84:185-193; Chu et al. (1997) *J. Exp. Med.* 186:1623-1631; Lipford.et al. (1997a) *Eur. J. Immunol.* 27:2340-2344; Lipford et al. (1997b) *Eur. J. Immunol.* 27:3420-3426; Weiner et al. (1997) *Proc. Natl. Acad. Sci. USA* 94:10833-10837; Macfarlane et al. (1997) *Immunology* 91:586-593; Schwartz et al. (1997) *J. Clin. Invest.* 100:68-73; Stein et al. (1997) *Antisense Technology*, Ch. 11 pp. 241-264, C. Lichtenstein and W. Nellen, Eds., IRL Press; Wooldridge et al. (1997) *Blood* 89:2994-2998; Leclerc et al. (1997) *Cell. Immunol.* 179:97-106; Kline et al. (1997) *J. Invest. Med.* 45(3):282A; Yi et al. (1998a) *J. Immunol.* 160: 1240-1245; Yi et al. (1998b) *J. Immunol.* 160:4755-4761; Yi et al. (1998c) *J. Immunol.* 160:5898-5906; Yi et al. (1998d) *J. Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J. Immunol.* 161:2428-2434; Krieg et al. (1998c) *Proc. Natl. Acad. Sci. USA* 95:12631-12636; Spiegelberg et al. (1998) *Allergy* 53(45S):93-97; Horner et al. (1998) *Cell Immunol.* 190:77-82; Jakob et al. (1998) *J. Immunol.* 161:3042-3049; Redford et al. (1998) *J. Immunol.* 161:3930-3935; Weeratna et al. (1998) *Antisense & Nucleic Acid Drug Development* 8:351-356; McCluskie et al. (1998) *J. Immunol.* 161(9):4463-4466; Gramzinski et al. (1998) *Mol. Med.* 4:109-118; Liu et al. (1998) *Blood* 92:3730-3736; Moldoveanu et al. (1998) *Vaccine* 16: 1216-1224; Brazolot Milan et al. (1998) *Proc. Natl. Acad. Sci. USA* 95:15553-15558; Broide et al. (1998) *J. Immunol.* 161:7054-7062; Broide et al. (1999) *Int. Arch. Allergy Immunol.* 118:453-456; Kovarik et al. (1999) *J. Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291-2298, WO 98/52962, WO 99/33488, WO 99/33868, WO 99/51259 and WO 99/62923. See also Zimmermann et al. (1998) *J. Immunol.* 160:3627-3630; Krieg (1999) *Trends Microbiol.* 7:64-65; U.S. Pat. Nos. 5,663,153, 5,723,335, 5,849,719 and 6,174,872. See also WO 99/56755, WO 00/06588, WO 00/16804; WO 00/21556; WO 00/67023 and WO 01/12223.

There exists a need in the art for effective treatments of acute and chronic hepatitis B and C.

All publications and patent applications cited herein are hereby incorporated by reference in their entirety.

DISCLOSURE OF THE INVENTION

The invention provides methods of suppressing and/or ameliorating hepatitis infection in an individual using immunostimulatory polynucleotide sequences. Accordingly, the invention provides methods for preventing, palliating, ameliorating, reducing, and/or eliminating one or more symptoms of HBV or HCV infection without administering HBV or HCV antigens. A polynucleotide comprising an immunostimulatory sequence (an ISS) is administered to an individual who has been exposed to HBV and/or HCV or is infected with HBV and/or HCV. The ISS-containing polynucleotide is administered without any HBV or HCV antigens (i.e., HBV or HCV antigen is not co-administered). Administration of the ISS results in reduced incidence and/or severity of one or more symptoms of HBV and/or HCV infection.

In one embodiment, the invention provides methods for preventing a symptom of acute hepatitis B virus (HBV) or hepatitis C virus (HCV) infection in an individual which entail administering an effective amount of a composition comprising a polynucleotide comprising an immunostimulatory sequence (ISS), (i.e., an amount of the composition sufficient to prevent a symptom of acute HBV or HCV infection) to the individual, wherein the ISS comprises the sequence 5'-C, G-3' and wherein an HBV or HCV antigen is not administered in conjunction with administration of the composition (i.e., antigen is not administered with the ISS-containing polynucleotide), thereby preventing a symptom of acute HBV or HCV infection. The individual may have been exposed to and/or infected by HBV or HVC.

Another embodiment of the invention provides methods of reducing severity of a symptom of acute HBV and/or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing severity of a symptom of acute HBV or HCV infection. The individual may have been exposed to and/or infected by HBV or HCV.

Another embodiment of the invention provides methods of delaying development of a symptom of acute HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby delaying development of a symptom of acute HBV or HCV infection. The individual may have been exposed to and/or infected by HBV and/or HCV.

Another embodiment of the invention provides methods of reducing duration of a symptom of acute HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing duration of a symptom of acute HBV or HCV infection. The individual may have been exposed to and/or infected by HBV and/or HCV.

Another embodiment of the invention provides methods for preventing a symptom of chronic HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby preventing a symptom of chronic HBV or HCV infection. The individual may have been exposed to and/or infected by HBV and/or HCV.

Another embodiment of the invention provides methods of reducing severity of a symptom of chronic HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing severity of a symptom of chronic HBV or HCV infection. The individual may have been exposed to and/or infected by HBV and/or HCV.

Another embodiment of the invention provides methods of delaying development of a symptom of chronic HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby delaying development of a symptom of chronic HBV or HCV infection. The individual may have been exposed to and/or infected by HBV and/or HCV.

Another embodiment of the invention provides methods of reducing duration of a symptom of chronic HBV or HCV infection in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing duration of a symptom of chronic HBV or HCV infection. The individual may have been exposed to and/or infected by HBV and/or HCV.

Another embodiment of the invention provides methods of suppressing an HBV or HCV infection in an individual infected with or at risk of being infected with HBV or HCV which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby suppressing an HBV or HCV infection.

In further aspect, the invention provides methods for reducing viremia in an individual exposed to and/or infected with HBV and/or HCV which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing HBV or HCV viremia.

In a further aspect, the invention provides methods for reducing blood levels of hepatitis virus antigens, preferably HBV or HCV antigens, in an individual which entail administering an effective amount of a composition comprising a polynucleotide comprising an ISS to the individual, wherein the ISS comprises the sequence 5'-C, G-3' and wherein an HBV or HCV antigen is not administered in conjunction with administration of the composition, thereby reducing blood levels of hepatitis virus antigens. The individual may have been exposed to and/or infected by HBV or HCV.

In another aspect, the invention provides kits for use in ameliorating a symptom of acute or chronic HBV or HCV infection in an individual exposed to and/or infected with HBV or HCV. The kits comprise a composition comprising a polynucleotide comprising an ISS, wherein the ISS comprises the sequence 5'-C, G-3', wherein the kit does not comprise an HBV or HCV antigen, and wherein the kits comprise instructions for administration of the composition to an individual infected with or exposed to HBV or HCV.

In some embodiments of the methods and kits of the invention, the ISS comprises the sequence 5'-purine, purine, C, G, pyrimidine, pyrimidine, C, G-3' or 5'-purine, purine, C, G, pyrimidine, pyrimidine, C, C-3'. In further embodiments of the methods and kits, the ISS comprises a sequence selected from the group consisting of AACGTTCC, AACGTTCG, GACGTTCC, and GACGTTCG.

In some embodiments of the methods and kits of the invention, the ISS comprises the sequence 5'-T, C, G-3'. In some embodiments of the methods and kits of the invention, the ISS comprises the sequence 5'-TGACTGTGAACGTTC-GAGATGA-3' (SEQ ID NO:1).

In some embodiments of the methods and kits of the invention, the individual is a mammal. In further embodiments, the mammal is human.

In some embodiments of the methods and kits of the invention, the virus is HBV.

In some embodiments of the methods and kits of the invention, the virus is HCV.

BRIEF DESCRIPTION OF THE DRAWINGS

FIG. 1(A) depicts results for STC mice injected with ISS at day 0, 7, and 14 (week 0, 1 and 2); FIG. 1(B) depicts results for STC mice injected with ISS at day 14 (week 2) only; FIG. 1(C) depicts results for STC mice injected with 100 ng of murine IL-12 on days 12, 13 and 14; and FIG. 1(D) depicts results for STC mice injected with phosphate buffered saline (PBS) on days 0, 7 and 14. Error bars indicate±one standard deviation (SD).

MODES FOR CARRYING OUT THE INVENTION

Figure 1:
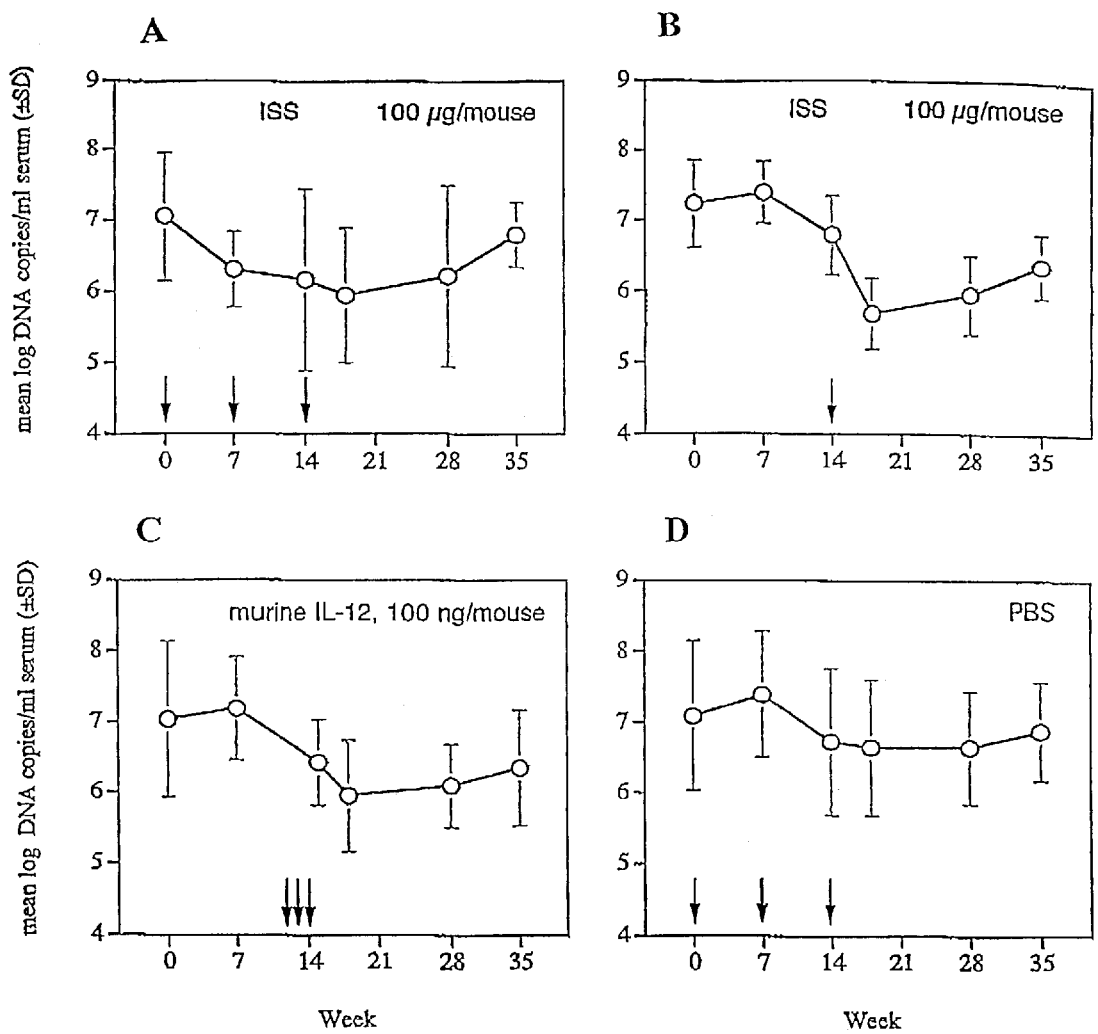
FIGS. 1(A)-(D) are graphs depicting effects of administration of ISS and control reagents to STC mice on viral titer. Results shown are blood viral DNA titer (in copies per milliliter) over time (in days).

We have discovered methods for the treatment of hepatitis B and C which are applicable to acute and/or chronic phases of infection. A polynucleotide comprising an immunostimulatory sequence (an "ISS") is administered to an individual exposed to and/or infected with hepatitis B virus (HBV) or hepatitis C virus (HCV). Administration of the ISS without co-administration of viral antigen, preferably without hepatitis antigen, results in reduced titer of hepatitis B as well as reduced HBV serum antigens in an animal model of chronic hepatitis B infection. We reasonably expect that such reduction would translate to reduction of severity of infection, including amelioration or even prevention of one or more symptoms associated with acute and/or chronic infection.

The invention also relates to kits for treatment and/or prevention of hepatitis B and/or hepatitis C infection in exposed individuals. The kits, which do not contain a hepatitis viral antigen, comprise a polynucleotide comprising an ISS and instructions describing the administration of an ISS to an individual for the intended treatment. Kits intended for use on individuals exposed to or infected with hepatitis B do not include hepatitis B viral antigens. Kits intended for use on individuals exposed to or infected with hepatitis C do not include hepatitis C viral antigens. Kits intended for use on individuals infected with both hepatitis B and hepatitis C contain neither hepatitis B nor hepatitis C viral antigens.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Weir & C. C. Blackwell, eds.); *Gene Transfer Vectors for Mammalian Cells*. (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993).

Definitions

The term "hepatitis B virus" or "HBV" is a term well-understood in the art and refers to a virus which is a member of the family hepadnaviridae, which family consists of the genus Orthohepadnavirus (hepadnaviruses which infect mammals) and Avihepadnaviridae (hepadnaviruses which infect birds). HBV is a Orthohepadnavirus which infects humans. Hepatitis B virus is a lipid-enveloped virus having a diameter of approximately 42 nm and comprises a circular, double stranded DNA genome. The genome is contained in a capsid which is enclosed by a lipid envelope studded with the surface, or "s", antigen (HBsAg). The 20 nm diameter particles are non-infectious. The main structural component of the 25-27 nm diameter capsid is the core or "c" protein (HBcAg). Also included in the capsid is a polymerase ("P protein"). The HBV genome encodes a number of additional products, including the "e" protein or "HBeAg", which is secreted by infected cells independently from the virion and other virion-related particles. Such antigens and/or antibodies against such antigens are generally diagnostic for HBV.

The term "hepatitis C virus" or "HCV" is a term well-understood in the art and refers to a virus which is the sole member of an unnamed genus of the family flaviviridae. Unlike most flaviviridae, HCV does not utilize a vector such as an insect, and humans are the only known host (although chimpanzees may be infected experimentally). Hepatitis C virus is a lipid-enveloped virus having a diameter of approximately 30-80 nm in diameter. Unlike HBV, HCV has a positive strand RNA genome. However, HCV does not integrate like a retrovirus. Serum titers of HCV tend to be relatively low, so most diagnostic assays rely on detecting patient antibodies to a viral protein such as the nucleocapsid protein or the NS3, NS4 and/or NS5 proteins. Additionally, diagnostic assays are available which detect genomic viral RNA.

The term "acute hepatitis infection", as used herein, refers to acute hepatitis B and/or acute hepatitis C infection, although not all individuals infected with HBV and/or HCV will exhibit clinical symptoms of acute hepatitis. Clinical symptoms of acute hepatitis include elevated bilirubin levels (up to an including frank jaundice), nausea, fatigue, elevated blood levels of liver enzymes (e.g., alanine aminotransferase or ALT and/or aspartate aminotransferase or AST), nausea, and joint and/or abdominal pain. Acute hepatitis may be the result of an initial infection by HBV or HCV, or may be the result of a "flare up" or relapse in a chronically infected patient. Acute hepatitis as a result of an initial infection by HBV or HCV may be distinguished from recurrent acute hepatitis by examination of anti-hepatitis virus immunoglobin. High levels of anti-virus IgM (and low levels of anti-virus IgG) are found in acute hepatitis due to an initial infection of HBV or HCV, while the reverse is found in relapsing or recurring acute hepatitis.

The term "chronic hepatitis", as used herein, refers to a disorder in which liver inflammation due to chronic HBV or HCV infection is present for at least six continuous months. Chronic hepatitis patients may suffer from fatigue, general malaise and/or abdominal pain. Chronic hepatitis due to HBV or HCV may be diagnosed by the use of diagnostic testing for the presence of HBV or HCV. Chronic hepatitis may be divided into two types (either or both of which are included in the invention), chronic active hepatitis and chronic persistent hepatitis. Chronic active hepatitis is hepatitis which is causing active damage to the liver, such as ongoing hepatocellular necrosis. Chronic persistent hepatitis is a hepatitis infection which is not currently causing damage, although pre-existing liver damage may be present. While the prognosis for patients with chronic persistent hepatitis is better than that for those with chronic active hepatitis, chronic persistent hepatitis may develop into chronic active hepatitis. The sequelae of chronic hepatitis include portal hypertension, cirrhosis, and hepatocellular carcinoma (HCC).

"Exposure" to a virus denotes encounter with HBV or HCV which allows infection, such as, for example, upon transfer of blood or a blood product from an infected individual such as by transfusion of contaminated blood, or a "needle stick" accident or incident involving a needle used on an HBV or HCV positive individual.

An individual is "seronegative" for a virus if antibodies specific to the virus cannot be detected in blood or serum samples from the individual using methods standard in the art, such as ELISA. Conversely, an individual is "seropositive" for a virus if antibodies specific for the virus can be detected in blood or serum samples from the individual using methods standard in the art, such as ELISA. An individual is said to "seroconvert" for a virus when antibodies to the virus can be detected in blood or serum from an individual who was previously seronegative.

A "symptom of HBV or HCV" refers to a symptom HBV and/or HCV infection. Such symptoms are well known in the art and include symptoms of acute and chronic hepatitis B and C. Symptoms of HBV or HCV include physical symptoms such as jaundice, abdominal pain, fatigue, malaise, nausea, and vomiting, as well as clinical/laboratory findings associated with hepatitis, such as elevated liver enzyme levels (e.g., alanine aminotransferase, ALT, aspartate aminotransferase, AST, and/or lactate dehydrogenase, LDH), elevated bilirubin, HBV and/or HCV viremia or antigen levels, portal hypertension, cirrhosis, anorexia, and other symptoms recognized in the art.

"Suppressing" hepatitis virus infection refers to any aspect of hepatitis B or C virus infection, such as a physical symptom (e.g., jaundice, fatigue, abdominal pain), a hepatitis-associated laboratory finding (e.g., liver enzyme levels in blood or cirrhosis), viral replication, or amount (titer) of virus, which is curtailed, inhibited, or reduced (in terms of severity and/or duration) in an individual or a population of individuals treated with an ISS-containing polynucleotide in accordance with the invention as compared to an aspect of viral infection in an individual or a population of individuals not treated in accordance with the invention. Reduction in viral titer includes, but is not limited to, elimination of the virus from an infected site or individual. Viral infection can be assessed by any means known in the art, including, but not limited to, detection of symptoms, measurement of liver function by laboratory testing, liver biopsy, direct or indirect measurement of liver portal vein pressure, and measurement of virus particles, viral nucleic acid or viral antigen titer and detection and/or measurement of anti-virus antibodies. Anti-virus antibodies are widely used to detect and monitor viral infection and generally are commercially available.

"Palliating" a disease or one or more symptoms of a disease or infection means lessening the extent and/or time course of undesirable clinical manifestations of a disease state or infection in an individual or population of individuals treated with an ISS in accordance with the invention.

As used herein, "delaying" development of viral infection or a symptom of hepatitis means to defer, hinder, slow, retard, stabilize, and/or postpone development of the disease or symptom when compared to not using the method(s) of the invention. This delay can be of varying lengths of time, depending on the history of the disease and/or individual being treated. As is evident to one skilled in the art, a sufficient or significant delay can, in effect, encompass prevention, in that the individual does not develop the disease.

"Reducing severity of a symptom" or "ameliorating a symptom" of viral infection means a lessening or improvement of one or more symptoms of hepatitis as compared to not administering an ISS-containing polynucleotide. "Reducing severity" also includes shortening or reduction in duration of a symptom. For hepatitis B and hepatitis C, these symptoms are well known in the art and include, but are not limited to, jaundice, abdominal pain, fatigue, malaise, nausea, and vomiting, as well as clinical/laboratory findings associated with hepatitis, such as elevated liver enzyme levels (e.g., ALT, AST, and/or LDH), elevated bilirubin, HBV and/or HCV viremia or antigen levels, portal hypertension, cirrhosis, anorexia, and other symptoms recognized in the art.

"Reducing duration of viral infection" means the length of time of viral infection (usually indicated by symptoms) is reduced, or shortened, as compared to not administering an ISS-containing polynucleotide.

"Preventing a symptom of infection" by a hepatitis virus means that the symptom does not appear after exposure to the virus.

The term "infected individual", as used herein, refers to an individual who has been infected by HBV and/or HCV. Symptoms of HBV infection include seropositivity for anti-HBsAg, HBeAg, or HBcAg, presence of HBsAg, HBeAg, or HBcAg in samples from the individual, or presence of HBV DNA in samples from the individual, as well as other symptoms known in the art. Symptoms of HCV infection include seropositivity for antibodies to nucleocapsid protein or the NS3, NS4 and/or NS5 proteins, presence of nucleocapsid protein or the NS3, NS4 and/or NS5 proteins in samples from the individual, or presence of HCV RNA or DNA in samples from the individual, as well as other symptoms known in the art.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Viral titer" is a term well-known in the art and indicates the amount of virus in a given biological sample. "Viremia" is a term well-known in the art as the presence of virus in the bloodstream and/or viral titer in a blood or serum sample. Amount of virus are indicated by various measurements, including, but not limited to, amount of viral nucleic acid; presence of viral particles (such as HBsAg or hepatitis B surface antigen particles); replicating units (RU); plaque forming units (PFU). Generally, for fluid samples such as blood and urine, amount of virus is determined per unit fluid, such as milliliters. For solid samples such as tissue samples, amount of virus is determined per weight unit, such as grams. Methods for determining amount of virus are known in the art and described herein.

An "individual" is a vertebrate, preferably a mammal, more preferably a human. Mammals include, but are not limited to, humans, farm animals, sport animals, rodents, primates and certain pets. Vertebrates also include, but are not limited to, birds (i.e., avian individuals) and reptiles (i.e., reptilian individuals).

The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$ T lymphocytes, B lymphocytes, and the like. Preferably, the ISS sequences preferentially activate a Th1-type response. A polynucleotide for use in methods of the invention contains at least one ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments.

"Adjuvant" refers to a substance which, when added to an immunogenic agent such as antigen, nonspecifically enhances or potentiates an immune response to the agent in the recipient host upon exposure to the mixture.

An "effective amount" or a "sufficient amount" of a substance is an amount sufficient to effect beneficial or desired results, including clinical results. An effective amount can be administered in one or more administrations. A "therapeutically effective amount" is an amount to effect beneficial clinical results, including, but not limited to, alleviation of one or more symptoms associated with viral infection as well as prevention of disease (e.g., prevention of one or more symptoms of infection).

A microcarrier is considered "biodegradable" if it is degradable or erodable under normal mammalian physiological conditions. Generally, a microcarrier is considered biodegradable if it is degraded (i.e., loses at least 5% of its mass and/or average polymer length) after a 72 hour incubation at 37° C. in normal human serum. Conversely, a microcarrier is considered "nonbiodegradable" if it is not degraded or eroded under normal mammalian physiological conditions. Generally, a microcarrier is considered nonbiodegradable if it not degraded (i.e., loses less than 5% of its mass and/or average polymer length) after at 72 hour incubation at 37° C. in normal human serum.

The term "immunostimulatory sequence-microcarrier complex" or "ISS-MC complex" refers to a complex of an ISS-containing polynucleotide and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the ISS.

As used herein, the term "comprising" and its cognates are used in their inclusive sense; that is, equivalent to the term "including" and its corresponding cognates.

As used herein, the singular form "a", "an", and "the" includes plural references unless indicated otherwise. For example, "a" symptom of viral infection includes one or more additional symptoms.

Methods of the Invention

The invention provides methods of ameliorating (i.e., reducing severity) and/or preventing one or more symptoms of acute and/or chronic HBV and HCV virus infection which may include reducing incidence. of or delaying of appearance of sequelae of HBV and/or HCV infection (i.e., cirrhosis or fulminant liver failure) by administering an ISS-containing polynucleotide (used interchangeably herein with "ISS") to an individual without administering a HBV or HCV antigen. The invention also provides methods of reducing viremia as well as methods of reducing levels of hepatitis viral antigen(s) in blood. Controlling and/or reducing viral load in an individual has several beneficial aspects, since hepatitis viruses not only cause acute disease but can also lead to chronic infection and other disease states. In addition, transmission of hepatitis B and C can occur through blood and blood products, perinatally and via sexual contact. The hepatitis virus may be HBV or HCV, although concurrent infections with both HBV and HCV may also be treated. It should be noted that hepatitis D virus infection may be present in individuals infected with HBV.

An ISS-containing composition which includes neither a HBV nor HCV antigen is administered to an individual exposed to, infected with, and/or exhibiting one or more symptoms of infection by HBV and/or HCV. Individuals receiving ISS are preferably mammals, more preferably humans. In accordance with the invention, neither HBV or HCV antigen is administered to the individual in conjunction with administration of an ISS (i.e., is not administered in a separate administration at or about the time of administration of the ISS).

In some embodiments, the individual has been exposed to HBV and/or HCV. An exposed individual can be easily identified by a skilled clinician or epidemiologist. Generally, an exposed individual is an individual that has been exposed to HBV and/or HCV by a route through which HBV and/or HCV can be transmitted. For example, an exposed individual may be a person who has been percutaneously exposed to blood or a blood product derived from an individual infected with HBV and/or HCV (e.g., by transfusion or by a "needle stick" accident). Alternately, the exposed individual may be a child born to an individual infected with HBV or HCV or the sexual partner of an HBV or HCV infected individual not practicing barrier methods of contraception.

In other embodiments, the individual is infected with HBV and/or HCV. Infection by HBV or HCV may be detected by diagnostic testing, or by clinical assessment of the infected individual. Because not all infected individuals exhibit overt symptoms of hepatitis, diagnostic assays which detect viral antigen(s), viral DNA or RNA, or host antibodies against viral antigen(s) are considered more reliable indicators of infection. Generally, HBsAg is a diagnostic antigen for HBV and the nucleocapsid, NS3, NS4 and/or NS5 proteins are diagnostic antigens for HCV. Infection is usually engendered by percutaneous exposure to blood or blood products from an infected individual, such as through transfusion, sharing of needles during intravenous drug use, or a "needle stick" incident, although sexual transmission and "vertical" transmission from mother to child during childbirth or the perinatal period are also routes for infection.

In some embodiments, the individual may have chronic or acute hepatitis B and/or hepatitis C. Acute hepatitis may be easily recognized by one of skill in the art, and is characterized by jaundice, fatigue, malaise, elevated blood levels of liver enzymes such as AST and/or ALT, dark urine and other symptoms known to those of skill in the art. However, as most types of hepatitis are characterized by these symptoms, positive diagnostic test for HBV or HCV is required to identify hepatitis B or hepatitis C, respectively. Chronic hepatitis B and hepatitis C are generally not characterized by any specific overt symptoms, although the sequelae of these disorders, such as hepatomegaly, disrupted clotting (due to reduced levels of clotting factors produced by the liver), ascites formation, cirrhosis, portal hypertension, and the like, are easily recognized by the clinician. However, altered liver function (as demonstrated by increased blood levels of liver enzymes) can be detected by laboratory testing. Additionally, chronic hepatitis B and hepatitis C sufferers may be subject to occasional "flare ups", in which the symptoms of acute hepatitis return.

ISS

The methods of this invention entail administering a polynucleotide comprising an ISS (or a composition comprising such a polynucleotide). In accordance with the present invention, the immunomodulatory polynucleotide contains at least one ISS, and can contain multiple ISSs. The ISSs can be adjacent within the polynucleotide, or they can be separated by additional nucleotide bases within the polynucleotide. Alternately, multiple ISSs may be delivered as individual polynucleotides.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995); Yamamoto et al. (1992); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-4575; Roman et al. (1997); and Lipford et al. (1997a).

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is unmethylated. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may comprise (i.e., contain one or more of) the sequence 5'-T, C, G-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrimidine, pyrimidine-3'.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 8; 10; 15; 20; 25; 30; 40; 50; 60; 75; 100; 125; 150; 175; 200; 250; 300; 350; 400; 500; 750; 1000; 2600; 5000; 7500, wherein the lower limit is less than the upper limit.

In some embodiments, the ISS comprises any of the following sequences:

GACGCTCC; GACGTCCC; GACGTTCC; GACGCCCC; AGCGTTCC;

AGCGCTCC; AGCGTCCC; AGCGCCCC; AACGTCCC; AACGCCCC;

AACGTTCC; AACGCTCC; GGCGTTCC; GGCGCTCC; GGCGTCCC;

GGCGCCCC; GACGCTCG; GACGTCCG; GACGCCCG; GACGTTCG;

AGCGCTCG; AGCGTTCG; AGCGTCCG; AGCGCCCG; AACGTCCG;

AACGCCCG; AACGTTCG; AACGCTCG; GGCGTTCG; GGCGCTCG;

GGCGTCCG; GGCGCCCG.

In some embodiments, the immunomodulatory polynucleotide comprises the sequence 5'

5'-TGACTGTGAACGTTCGAGATGA-3'. (SEQ ID NO:1)

In some embodiments, the ISS comprises any of the following sequences:

GACGCU; GACGUC; GACGUU; GACGUT; GACGTU; AGCGUU;

AGCGCU; AGCGUC; AGCGUT; AGCGTU; AACGUC; AACGUU;

AACGCU; AACGUT; AACGTU; GGCGUU; GGCGCU; GGCGUC;

GGCGUT; GGCGTU.

In some embodiments, the ISS comprises any of the following sequences:

GABGCTCC; GABGTCCC; GABGTTCC; GABGCCCC; AGBGTTCC;

AGBGCTCC; AGBGTCCC; AGBGCCCC; AABGTCCC; AABGCCCC;

AABGTTCC; AABGCTCC; GGBGTTCC; GGBGCTCC; GGBGTCCC;

GGBGCCCC; GABGCTCG; GABGTCCG; GABGCCCG; GABGTTCG;

AGBGCTCG; AGBGTTCG; AGBGTCCG; AGBGCCCG; AABGTCCG;

AABGCCCG; AABGTTCG; AABGCTCG; GGBGTTCG; GGBGCTCG;

GGBGTCCG; GGBGCCCG; GABGCTBG; GABGTCBG; GABGCCBG;

GABGTTBG; AGBGCTBG; AGBGTTBG; AGBGTCBG; AGBGCCBG;

AABGTCBG; AABGCCBG; AABGTTBG; AABGCTBG; GGBGTTBG;

GGBGCTBG; GGBGTCBG; GGBGCCBG, where B is 5-bromocytosine.

In some embodiments, the ISS comprises any of the following sequences:

GABGCUCC; GABGUCCC; GABGUTCC; GABGTUCC; GABGUUCC;

AGBGUUCC; AGBGTUCC; AGBGUTCC; AGBGCUCC; AGBGUCCC;

AABGUCCC; AABGUUCC; AABGUTCC; AABGTUCC; AABGCUCC;

GGBGUUCC; GGBGUTCC; GGBGTUCC; GGBGCUCC; GGBGUCCC;

GABGCUCG; GABGUCCG; GABGUUCG; GABGUTCG; GABGTUCG;

AGBGCUCG; AGBGUUCG; AGBGUTCG; AGBGTUCG; AGBGUCCG;

AABGUCCG; AABGUUCG; AABGUTCG; AABGTUCG; AABGCUCG;

GGBGUUCG; GGBGUTCG; GGBGTUCG; GGBGCUCG; GGBGUCCG;

GABGCUBG; GABGUCBG; GABGUUBG; GABGUTBG; GABGTUBG;

AGBGCUBG; AGBGUUBG; AGBGUCBG; AGBGUTBG; AGBGTUBG;

AABGUCBG; AABGUUBG; AABGUTBG; AABGTUBG; AABGCUBG;

GGBGUUBG; GGBGUTBG; GGBGTUBG; GGBGCUBG; GGBGUCBG, where B is 5-bromocytosine.

In other embodiments, the ISS comprises any of the sequences:

```
5'-TGACCGTGAACGTTCGAGATGA-3';      (SEQ ID NO:2)

5'-TCATCTCGAACGTTCCACAGTCA-3';     (SEQ ID NO:3)

5'-TGACTGTGAACGTTCCAGATGA-3';      (SEQ ID NO:4)

5'-TCCATAACGTTCGCCTAACGTTCGTC-3';  (SEQ ID NO:5)

5'-TGACTGTGAABGTTCCAGATGA-3',      (SEQ ID NO:6)
``` where B is 5-bromocytosine;

```
5'-TGACTGTGAABGTTCGAGATGA-3',      (SEQ ID NO:7)
``` where B is 5-bromocytosine and

```
5'-TGACTGTGAABGTTBGAGATGA-3',      (SEQ ID NO:8)
``` where B is 5-bromocytosine.

An ISS and/or ISS-containing polynucleotide may contain modifications. Modifications of ISS include any known in the art, but are not limited to, modifications of the 3'-OH or 5'-OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-broniocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably beta plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in *Protocols for Oligonucleotides and Analogs, Synthesis and Properties* (Agrawal, ed.) Humana Press, Totowa, N.J.; Warner et al. (1984) DNA 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in *Oligonucleotides as Therapeutic Agents*, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in *Protocols for Oligonucleotides and Analogs, Synthesis and Properties* (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141).

Oligonucleotides with phosphorothioate backbones can be more immunogenic than those with phosphodiester backbones and appear to be more resistant to degradation after injection into the host. Braun et al. (1988) *J. Immunol.* 141: 2084-2089; and Latimer et al. (1995) *Mol. Immunol.* 32:1057-1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo [2,3-d]pyrimidin-5-yl, 2-amino-4-oxopyrrolo[2.3-d]pyrimidin-3-yl groups, where the purines are attached to the sugar 'moiety of the ISS via the 9-position, the pyrimidines via the 1-position, the pyrrolopyrimidines via the 7-position and the pyrazolopyrimidines via the 1-position.

The ISS may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

The ISS used in the methods of the invention may be produced as ISS-microcarrier complexes. ISS-microcarrier complexes comprise an ISS-containing polynucleotide bound to a microcarrier (MC). ISS-MC complexes comprise an ISS bound to the surface of a microcarrier (i.e., the ISS is not encapsulated in the MC), adsorbed within a microcarrier (e.g., adsorbed to PLGA beads), or encapsulated within a MC (e.g., incorporated within liposomes).

ISS-containing oligonucleotides bound to microparticles (SEPHAROSE® beads) have previously been shown to have immunostimulatory activity in vitro (Liang et al., (1996), *J. Clin. Invest.* 98:1119-1129). However, recent results show that ISS-containing oligonucleotides bound to gold, latex and magnetic particles are not active in stimulating proliferation of 7TD1 cells, which proliferate in response to ISS-containing oligonucleotides (Manzel et al., (1999), *Antisense Nucl. Acid Drug Dev.* 9:459-464).

Microcarriers are not soluble in pure water, and are less than about 50-60 µm in size, preferably less than about 10 µm in size, more preferably from about 10 nm to about 10 µm, 25 nm to about 5 µm, 50 nm to about 4.5 µm or 1.0 µm to about 2.0 µm in size. Microcarrers may be any shape, such as spherical, ellipsoidal, rod-shaped, and the like, although spherical microcarriers are normally preferred. Preferred microcarriers have sizes of or about 50 nm, 200 nm, 1 µm, 1.2 µm, 1.4 µm, 1.5 µm, 1.6 µm, 1.8 µm, 2.0 µm, 2.5 µm or 4.5 µm. The "size" of a microcarier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ±about 5-10% of the stated measurement. Size characteristics may also be determined by dynamic light scattering. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

Microcarriers may be solid phase (e.g., polystyrene beads) or liquid phase (e.g., liposomes, micelles, or oil droplets in an oil and water emulsion). Liquid phase microcarriers include liposomes, micelles, oil droplets and other lipid or oil-based particles. One preferred liquid phase microcarrier is oil droplets within an oil-in-water emulsion. Preferably, oil-in-water emulsions used as microcarriers comprise biocompatible substituents such as squalene. Liquid phase microcarriers are normally considered nonbiodegradable, but may be biodegradable liquid phase microcarriers may be produced by incorporation of one or more biodegradable polymers in the liquid microcarrier formulation. In one preferred embodiment, the microcarrier is oil droplets in an oil-in-water emulsion prepared by emulsification of squalene, sorbitan trioleate, TWEEN 80® in an aqueous pH buffer.

Solid phase microcarriers for use in ISS-microcarrier complexes may be made from biodegradable materials or nonbiodegradable materials, and may include or exclude agarose or modified agarose microcarriers. Useful solid phase biodegradable microcarriers include, but are not limited to: biodegradable polyesters, such as poly(lactic acid), poly(glycolic acid), and copolymers (including block copolymers) thereof, as well as block copolymers of poly(lactic acid) and poly (ethylene glycol); polyorthoesters such as polymers based on 3,9-diethylidene-2,4,8,10-tetraoxaspiro[5.5]undecane (DETOSU); polyanhydrides such as poly(anhydride) polymers based on sebacic acid, p-(carboxyphenoxy)propane, or p-(carboxyphenoxy)hexane; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al. (1996) *Biotechnol. Bioeng.* 1996:102); and polyamides such as poly(lactic acid-co-lysine). A wide variety of nonbiodegradable materials suitable for manufacturing microcarriers are also known, including, but not limited to polystyrene, polyethylene, latex, gold, and ferromagnetic or paramagnetic materials. Solid phase microcarriers may be covalently modified to incorporate one or more moieties for use in linking the ISS, for example by addition of amine groups for covalent linking using amine-reactive crosslinkers.

The ISS-microcarrier complexes may be covalently or non-covalently linked. Covalently linked ISS-MC complexes may be directly linked or be linked by a crosslinking moiety of one or more atoms (typically the residue of a crosslinking agent). The ISS may be modified to allow or augment binding to the MC (e.g., by incorporation of a free sulfhydryl for covalent crosslinking or addition of a hydrophobic moieties such as lipids, steroids, sterols such as cholesterol, and terpenes, for hydrophobic bonding), although unmodified ISS may be used for formation of non-covalent ISS-MC complex formation by electrostatic interaction or by base pairing (e.g., by base pairing at least one portion of the ISS with a complementary oligonucleotide bound to the microcarrier). ISS-containing polynucleotides may be linked to solid phase microcarriers or other chemical moieties to facilitate ISS-MC complex formation using conventional technology known in the art, such as use of available heterobifunctional crosslinkers (e.g., succinimidyl 4-(N-maleimidomethyl)cyclohexane-1-carboxylate or its sulfo-derivatives for covalently linking an amine-derivatized microcarrier and an ISS modified to contain a free sulfhydryl) or by addition of compounds such as cholesterol (e.g., by the method of Godard et al. (1995) *Eur. J. Biochem.* 232:404-410) to facilitate binding to hydrophobic microcarriers such as oil droplets in oil-in-water emulsions. Alternatively, modified nucleosides or nucleotides, such as are known in the art, can be incorporated at either terminus, or at internal positions in the ISS. These can contain blocked functional groups which, when deblocked, are reactive with a variety of functional groups which can be present on, or attached to, the microcarrier or a moiety which would facilitate binding to a microcarrier. Certain embodiments of noncovalently linked ISS-MC complexes utilize a binding pair (e.g., an antibody and its cognate antigen or biotin and streptavidin or avidin), where one member of the binding pair is bound to the ISS and the microcarrier is derivatized with the other member of the binding pair (e.g., a biotinylated ISS and a streptavidin-derivatized microcarrier may be combined to form a noncovalently linked ISS-MC complex).

Non-covalent ISS-MC complexes bound by electrostatic binding typically exploit the highly negative charge of the polynucleotide backbone. Accordingly, microcarriers for use in non-covalently bound ISS-MC complexes are generally positively charged at physiological pH (e.g., about pH 6.8-7.4). The microcarrier may intrinsically possess a positive charge, but microcarriers made from compounds not normally possessing a positive charge may be derivatized or otherwise modified to become positively charged. For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles.

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vaccum, before storing at 4° C.

Generally, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

Physico-chemical characteristics such as mean size, size distribution and surface charge of dried microspheres may be determined. Size characteristics are determined, for example, by dynamic light scattering technique and the surface charge was determined by measuring the zeta potential.

Generally, ISS-containing polynucleotides can be adsorbed onto the cationic microspheres by overnight aqueous incubation of ISS and the particles at 4° C. Microspheres are characterized for size and surface charge before and after ISS association. Selected batches may then evaluated for activity as described herein.

Administration

An ISS-containing polynucleotide may be administered after exposure to HBV and/or HCV and/or after infection by HBV and/or HCV. In certain instances, the ISS-containing polynucleotide may be administered to an infected individual in the absence of physical symptoms of viral infection (e.g., jaundice, fatigue, etc.). Accordingly, administration of ISS-containing polynucleotide may be at various times with respect to exposure to, infection by and/or onset of symptoms of infection by HBV and/or HCV. Additionally, treatments employing an ISS-containing polynucleotide may also be employed in conjunction with other treatments or as 'second line' treatments employed after failure of a 'first line' treatment (e.g., ISS-containing polynucleotide therapy may be employed after failure of interferon therapy). Further, an ISS-containing polynucleotide may be administered in a single dose or in multiple doses. If the ISS-containing polynucleotide is administered on multiple occasions, the ISS may be administered on any schedule selected by the clinician, such as daily, every other day, every three days, every four days, every five days, every six days, weekly, biweekly, monthly or at ever longer intervals (which may or may not remain the same during the course of treatment). Where multiple administrations are given, the ISS-containing polynucleotide may be given in 2, 3, 4, 5,6, 7, 8, 9, 10 or more separate administrations.

In some embodiments, when ISS-containing polynucleotide is administered to an individual who has been exposed to HBV and/or HCV, ISS-containing polynucleotide may be administered prior to the appearance of physical symptom(s) of HBV and/or HCV. ISS-containing polynucleotide is preferably administered to an individual exposed to HBV and/or HCV less than about 28, 21, or 14 days after exposure to HBV and/or HCV, preferably less than about 10 days after exposure to HBV and/or HCV, more preferably less than about 7 days after exposure to HBV and/or HCV, even more preferably less than about 5 days after exposure to HBV and/or HCV. In some embodiments, ISS-containing polynucleotide is administered about 3 days after exposure to HBV and/or HCV. In other embodiments, the ISS-containing polynucleotide is administered as soon as possible following a known exposure (e.g., after a needle stick or other percutaneous exposure to a bodily fluid or other material known or thought to be contaminated with HBV and/or HCV). In such embodiments, the ISS-containing polynucleotide is preferably administered within 48, 36, 24, or 12 hours after exposure.

In another embodiment, the ISS-containing polynucleotide is administered upon or after appearance of at least one symptom of HBV or HCV infection. Preferably, ISS-containing polynucleotide is administered within about 28, 21, 14, 7, 5 or 3 days following appearance of a symptom of HBV and/or HCV infection. However, some infected individuals exhibiting symptoms will already have undertaken one or more courses of treatment with another therapy (e.g., interferon-based therapy). In such individuals, or in individuals who failed to appreciate the import of their symptoms, the ISS-containing polynucleotide may be administered at any point following infection.

Some individuals infected with HBV and/or HCV are asymptomatic, and identified through routine screening (e.g., when donating blood). Accordingly, for individuals presenting without appreciable or noticeable physical symptoms, the ISS-containing polynucleotide may be administered at any point following infection.

ISS polynucleotides may be formulated in any form known in the art, such as dry powder, semi-solid or liquid formulations. For parenteral administration ISS polynucleotides preferably administered in a liquid formulation, although solid or semi-solid formulations may also be acceptable, particularly where the ISS polynucleotide is formulated in a slow release depot form.

ISS polynucleotide formulations may contain additional components such as salts, buffers, bulking agents, osmolytes, antioxidants, detergents, surfactants and other pharmaceutically-acceptable excipients as are known in the art. Generally, liquid ISS polynucleotide formulations made in USP water for injection and are sterile, isotonic and pH buffered to a physiologically-acceptable pH, such as about pH 6.8 to 7.5.

ISS-containing polynucleotides may be formulated in delivery vehicles such as liposomes, oil/water emulsion or slow release depot formulations. Methods of formulating polynucleotides in such forms are well known in the art.

ISS-containing polynucleotide formulations may also include or exclude immunomodulatory agents such as adjuvants and immunostimulatory cytokines, which are well lnown in the art.

A suitable dosage range or effective amount is one that provides the desired reduction of symptom(s) and/or suppression of viral infection and depends on a number of factors, including the particular hepatitis virus, ISS sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for an ISS-containing polynucleotide of about 20 bases, a dosage range may be selected from, for example, an independently selected lower limit such as about 0.1, 0.25, 0.5, 1, 2, 5, 10, 20, 30 40, 50 60, 80, 100, 200, 300, 400 or 500 µg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 µg/kg. For example, a dose may be about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg, 500 to 1000 µg/kg, 500 to 5000 µg/kg, or 500 to 10,000 µg/kg. Generally, parenteral routes of administration require higher doses of ISS compared to more direct application to infected tissue, as do ISS-containing polynucleotides of increasing length.

Polynucleotides comprising an ISS may be administered by systemic (e.g., parenteral) or local/regional administration, although systemic administration is preferred, due to the relative inaccessability of the site of infection. For local/regional administration, polynucleotides comprising an ISS may be administered into the portal vein, but this route of administration is not preferred because of the invasiveness of the procedure.

In other embodiments, the ISS-containing polynucleotide is administered parepterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used in accordance with the invention.

Nasopharyngeal and pulmonary routes of administration include, but are not limited to, intranasal, inhalation, transbronchial and transalveolar routes. The ISS-containing polynucleotide may thus be administered by inhalation of aerosols, atomized liquids or powders. Devices suitable for administration by inhalation of ISS-containing compositions include, but are not limited to, nebulizers, atomizers, vaporizers, and metered-dose inhalers. Nebulizers, atomizers, vaporizers and metered-dose inhalers filled with or employing reservoirs containing formulations comprising the ISS-containing polynucleotide(s) are among a variety of devices suitable for use in inhalation delivery of the ISS-containing polynucleotide(s). Other methods of delivering to respiratory mucosa include delivery of liquid formulations, such as by nose drops.

IV, IP, IM and ID administration may be by bolus or infusion administration. For SC administration, administration may be by bolus, infusion or by implantable device, such as an implantable minipump (e.g., osmotic or mechanical minipump) or slow release implant. The ISS polynucleotide(s) may also be delivered in a slow release formulation adapted for IV, IP, IM, ID or SC administration. Administration by inhalation is preferably accomplished in discrete doses (e.g., via a metered dose inhaler), although delivery similar to an infusion may be accomplished through use of a nebulizer. Administration via the transdermal and transmucosal routes may be continuous or pulsatile.

Assessment

In some embodiments, administration of an ISS-containing polynucleotide results in prevention, palliation, and/or improvement in one or more symptoms of HBV or HCV. The exact form of prevention, palliation or improvement will depend on the particular hepatitis virus, the symptoms experienced by the patient, and the stage of the hepatitis, but includes reduction or improvement in one or more physical symptoms such as jaundice, fatigue, abdominal pain and the like and/or clinical/laboratory findings associated with hepatitis such as viremia, blood levels of liver enzymes, portal hypertension, cirrhosis, and the like.

Symptoms of infection may be assessed before and/or after administration of ISS-containing polynucleotide. As will be apparent to one of skill in the art, the symptoms measured and the method of their measurement will vary depending on the particular hepatitis virus and the stage of infection. Physical symptoms of acute HBV and/or HCV infection include jaundice, fatigue, abdominal pain, dark urine, and other symptoms known in the art. Subjective physical symptoms such as abdominal pain and fatigue may be measured on a qualitative (e.g., presence/absence) basis or may be quantitated using a visual scale system. Jaundice may also be measured on a qualitative basis or may be quantitated by measurement of blood or serum levels of bilirubin.

Clinical/laboratory findings associated with hepatitis are normally measured through clinical assessment, diagnostic assays, and histologic testing. For example, blood/serum levels of liver enzymes may be quantitated by running a standard clinical laboratory liver function panel of tests which include quantitation of AST and ALT levels in the individual's blood or serum. Viremia (i.e., viral titer in a blood or serum sample) may be measured by any method known in the art, such as quantitation of viral particles (for example, by isolation and visualization or by assay of DNase resistant particles), detection of viral antigens in blood or serum samples, detection of antivirus antibodies in blood or serum samples and/or detection of viral nucleic acid (e.g., by PCR amplification using HBV or HCV specific primers or by in situ hybridization with virus-specific probes). Viral titer may also be measured in liver tissue biopsies, generally by quantitation of viral nucleic acid, although viral antigens may also be used for calculation of viral titer. Viral titer from tissue samples is calculated in virus particles per unit weight of tissue.

Kits of the Invention

The invention provides kits for carrying out the methods of the invention (i.e., treatment and/or prevention of HBV and/or HCV infection). Accordingly, a variety of kits are provided. The kits may be used for any one or more of the following (and, accordingly, may contain instructions for any one or more of the following uses): reducing levels of a hepatitis B and/or hepatitis C antigen in blood in an individual who has been infected with hepatitis B and/or hepatitis C; reducing viremia in an individual infected with or exposed to hepatitis B and/or hepatitis C; preventing one or more symptoms of hepatitis B and/or hepatitis C infection in an individual exposed to hepatitis B, hepatitis C, or both hepatitis B and C; reducing severity of one or more symptoms of hepatitis B and/or hepatitis C infection in an individual who has been infected with hepatitis B, hepatitis C, or both hepatitis B and C; delaying development of one or more symptoms of hepatitis B and/or hepatitis C infection in an individual who has been infected with hepatitis B, hepatitis C, or both hepatitis B and C; reducing duration of one or more symptoms of hepatitis B and/or hepatitis C infection in an individual who has been infected with hepatitis B, hepatitis C, or both hepatitis B and C; reducing severity of one or more symptoms of chronic hepatitis B and/or hepatitis C infection in an individual infected with hepatitis B, hepatitis C, or both hepatitis B and C; preventing of one or more symptoms of chronic hepatitis B and/or hepatitis C infection in an individual who has been infected with hepatitis B, hepatitis C, or both hepatitis B and C; delaying development of one or more symptoms of chronic hepatitis B and/or hepatitis C infection in an individual who has been infected with hepatitis B, hepatitis C, or both hepatitis B and C; reducing duration of one or more symptoms of chronic hepatitis B and/or hepatitis C infection in an individual who has been infected with hepatitis B, hepatitis C, or both hepatitis B and C. As is understood in the art, any one or more of these uses would be included in instructions directed to treating or preventing hepatitis B and/or hepatitis C infection.

The kits of the invention comprise one or more containers comprising an ISS-containing polynucleotide and a set of instructions, generally written instructions although electronic storage media (e.g., magnetic diskette or optical disk) containing instructions are also acceptable, relating to the use and dosage of the ISS-containing polynucleotide for the intended treatment (e.g., reducing levels of a hepatitis B and/or hepatitis C antigen in blood in an individual who has been infected with hepatitis B and/or hepatitis C; reducing viremia in an individual infected with or exposed to hepatitis B and/or hepatitis C; preventing one or more symptoms of hepatitis B and/or hepatitis C infection in an individual exposed to hepatitis B, hepatitis C, or both hepatitis B and C; reducing severity of one or more symptoms of hepatitis B and/or hepatitis C infection in an individual who has been infected with hepatitis B, hepatitis C, or both hepatitis B and C; delaying development of one or more symptoms of hepatitis B and/or hepatitis C infection in an individual who has been infected with hepatitis B, hepatitis C, or both hepatitis B and C; reducing duration of one or more symptoms of hepatitis B and/or hepatitis C infection in an individual who has been infected with hepatitis B, hepatitis C, or both hepatitis B and C; reducing severity of one or more symptoms of chronic hepatitis B and/or hepatitis C infection in an individual infected with hepatitis B, hepatitis C, or both hepatitis B and C; preventing one or more symptoms of chronic hepatitis B and/or hepatitis C infection in an individual infected with hepatitis B, hepatitis C, or both hepatitis B and C; delaying development of one or more symptoms of chronic hepatitis B and/or hepatitis C infection in an individual infected with hepatitis B, hepatitis C, or both hepatitis B and C and/or reducing duration of one or more symptoms of chronic hepatitis B and/or hepatitis C infection in an individual infected with hepatitis B, hepatitis C, or both hepatitis B and C). The instructions included with the kit generally include information as to dosage, dosing schedule, and route of administration for the intended treatment. The containers of ISS may be unit doses, bulk packages (e.g., multi-dose packages) or sub-unit doses.

The kits of the invention do not include any packages or containers which contain viral antigens from the hepatitis virus(es) the kit is intended to be used to treat. Accordingly, neither the container comprising the ISS-containing polynucleotide nor any other containers in the kit contain hepatitis B viral antigens in kits intended for use on individuals exposed to or infected with hepatitis B, neither the container comprising the ISS-containing polynucleotide nor any other containers in the kit contain hepatitis C viral antigens in kits intended for use on individuals exposed to or infected with hepatitis C, and neither the container comprising the ISS-containing polynucleotide nor any other containers in the kit contain hepatitis B or C viral antigens in kits intended for use on individuals infected with both hepatitis B and hepatitis C.

The ISS component of the kit may be packaged in any convenient, appropriate packaging. For example, if the ISS is a freeze-dried formulation, an ampoule with a resilient stopper is normally used, so that the drug may be easily reconstituted by injecting fluid through the resilient stopper. Ampoules with non-resilient, removable closures (e.g., sealed glass) or resilient stoppers are most conveniently used for injectable forms of ISS. Also, prefilled syringes may be used when the kit is supplied with a liquid formulation of the ISS-containing polynucleotide. Also contemplated are packages for use in combination with a specific device, such as an inhaler, nasal administration device (e.g., an atomizer) or an infusion device such as a minipump.

As stated above, any ISS-containing polynucleotide described herein may be used, such as, for example, any polynucleotide comprising any of the following ISS: the sequence 5'-cytosine, guanine-3', the sequence 5'-T, C, G-3', the sequence 5'-C, G, pyrimidine, pyrimidine, C, G-3', the sequence 5'-purine, purine, C, G, pyrimidine, pyrimidine, C, G-3', the sequence 5'-purine, purine, C, G, pyrimidine, pyrimidine, C, C-3'; the sequence SEQ ID NO: 1018; the sequence 5'-purine, purine, B, G, pyrimidine, pyrimidine-3' wherein B is 5-bromocytosine or the sequence 5'-purine, purine, B, G, pyrimidine, pyrimidine, C, G-3' wherein B is 5-bromocytosine.

The following Examples are provided to illustrate, but not limit, the invention.

EXAMPLES

Example 1

Administration of an ISS in an Animal Model of Chronic HBV Infection

ISS activity was tested in an animal model of chronic hepatitis. An ISS-containing phosphorothioate oligonucleotide (5'-TGACTGTGAACGTTCGAGATGA-3') (SEQ ID NO:1), was delivered to STC strain transgenic mice, followed by measurement of HBV DNA and HBsAg production.

STC line mice were developed at Stanford University by Patricia Marion. The majority of these mice secrete HBV of the Ayw genotype (Galibert et al. (1979) Nature 281:646) to titers of $10^{6-8}$ viral genome equivalents per ml of serum. STC mice were derived from the FVB strain, and were constructed by microinjection of HBV genomic DNA. STC mice have been shown to be responsive to drugs which inhibit HBV replication, and so are considered a good model of chronic HBV.

Approximately one month old mice were bled and tested for serum levels of HBsAg, which is predictive of viral DNA titer. A pool of 40 STC mice with approximately equal levels of HBsAg were selected and randomly assigned to four treatment groups of 10 animals each. The groups were treated as follows:

1. 100 µg of ISS injected subcutaneously, once per week for 3 weeks (days 0, 7, 14)
2. 100 µg of ISS injected subcutaneously, one injection at day 14
3. 100 ng of murine 1L-12 injected intraperitoneally on days 12, 13, and 14.
4. PBS injected subcutaneously (days 0, 7, 14)

Blood samples were taken at day 0, 7, 14, 15 (22 hr after last IL-12 injection), 18, 28 and 35. Serum prepared from the blood samples was tested for HBV DNA by quantitative PCR (testing performed under contract by Hepadnavirus Testing, Inc.), and HBsAg using a commercially available EIA kit for HBsAg from Abbott Laboratories. Animals were sacrificed at day 35 and livers were collected for histologic analysis.

The results of the quantitative PCR assays for serum HBV DNA levels in HBV-producing mice treated with ISS, murine IL-12 or PBS, are summarized in FIG. 1. The results are plotted as means of the HBV DNA levels of each of the 4 groups in each of the serial samples. Samples were blinded to the person conducting the assays. Both ISS and murine IL-12 were effective in reducing viral titer in STC mice. The most dramatic titer drop was seen in Group 2 (single subcutaneous injection of ISS at day 14), where the mean viral DNA titer was reduced by 90 fold three days after injection.

Figure 2:
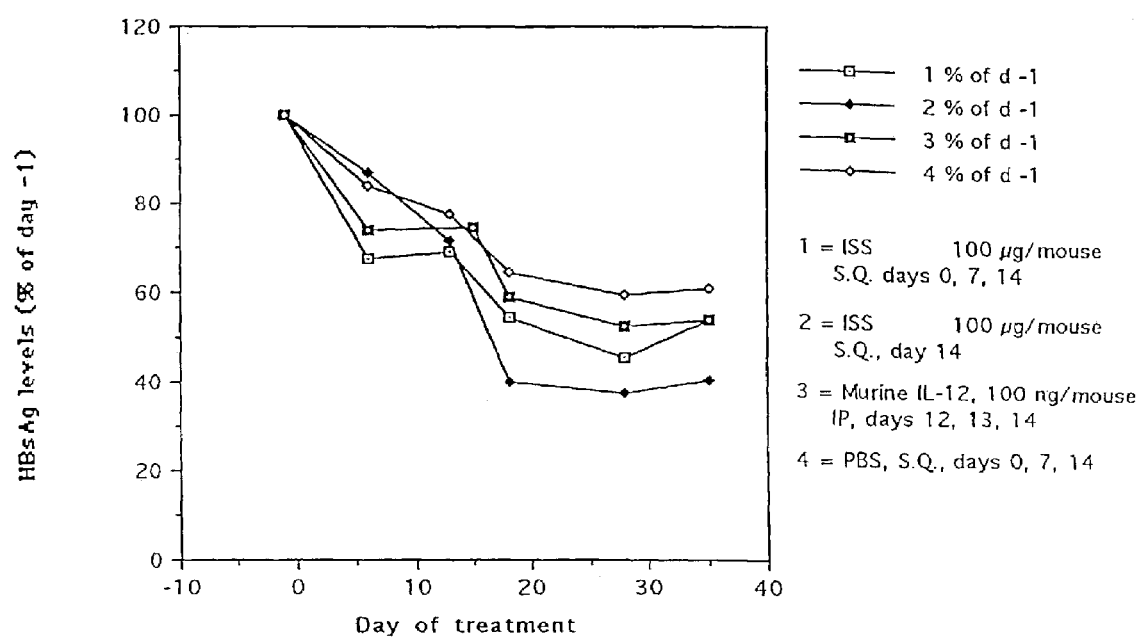
FIG. 2 is a graph depicting effects of administration of ISS and control reagents to STC mice on hepatitis B surface antigen (HBsAg) levels. Results are shown as percent of value at day-1 over time (in days). Open squares indicate results for STC mice injected with ISS at day 0, 7, and 14 (week 0, 1 and 2); closed diamonds indicate results for STC mice injected with ISS at day 14 (week 2) only; closed square indicate results for STC mice injected with 100 ng of murine IL-12 on days 12, 13 and 14; and open diamonds indicate results for STC mice injected with phosphate buffered saline on days 0, 7 and 14.

The results of the assays for serum HBsAg levels in HBV-producing mice treated with ISS, murine IL-12 or PBS are summarized in FIG. 2. The results are plotted as averages of the antigen levels of each of the 4 groups in each of the serial sample. The data showed a trend towards decreased average HBsAg values of animals treated with ISS compared to control animals treated with PBS.

It should be noted that, as with all lineages of HBV-producing mice, some animals sharply dropped titer during the observation period, even before treatments, or with treatment with the control. Despite the randomizing at −7 days, more of these mice were found in groups 3 and 4 (IL-12 and control, respectively), possibly obscuring a more dramatic effect by the ISS.

The present invention has been detailed both by direct description and by example. Equivalents and modifications of the present invention will be apparent to those skilled in the art, and are encompassed within the scope of the invention.

What is claimed is:

1. A method of reducing the viral titer of a hepatitis C virus (HCV) in a human infected with HCV, comprising administering a composition comprising a polynucleotide comprising an immunostimulatory sequence (ISS) to said human infected with HCV, wherein the ISS comprises the sequence

5'-AACGTTCG-3', wherein the polynucleotide is greater than 8 and less than about 50 nucleotides in length, wherein an HCV antigen is not administered in conjunction with administration of said composition, and wherein said composition is administered in an amount sufficient to reduce said viral titer.

2. The method of claim 1, wherein the ISS comprises the sequence

5'-TGACTGTGAACGTTCGAGATGA-3'    (SEQ ID NO:1).

3. The method of claim 1, wherein administration is intravenous or subcutaneous.

4. The method of claim 1, wherein the polynucleotide is greater than 10 and less than about 50 nucleotides in length.

5. The method of claim 1, wherein the ISS is administered in conjunction with other treatments.

* * * * *

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 1
tgactgtgaa cgttcgagat ga                                         22

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgaccgtgaa cgttcgagat ga                                         22

<210> SEQ ID NO 3
<211> LENGTH: 23
<212> TYPE: DNA
<213> ORGANISM: Artificial Sequence
<220> FEATURE:
<223> OTHER INFORMATION: Polynucleotide containing CG

<400> SEQUENCE: 3
tcatctcgaa cgttccacag tca                                        23

<210> SEQ ID NO 4
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 4
tgactgtgaa cgttccagat ga                                         22

<210> SEQ ID NO 5
<211> LENGTH: 26
<212> TYPE: DNA
<213> ORGANISM: Artificial Sequence
<220> FEATURE:
<223> OTHER INFORMATION: Polynucleotide containing CG

<400> SEQUENCE: 5
tccataacgt tcgcctaacg ttcgtc                                     26

<210> SEQ ID NO 6
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n = 5-bromocytosine

<400> SEQUENCE: 6
tgactgtgaa ngttccagat ga                                         22

```
<210> SEQ ID NO 7
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n = 5-bromocytosine

<400> SEQUENCE: 7
tgactgtgaa ngttcgagat ga                                             22

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11, 15
<223> OTHER INFORMATION: n = 5-bromocytosine

<400> SEQUENCE: 8
tgactgtgaa ngttngagat ga                                             22
```